United States Patent [19]
Whitlow et al.

[11] Patent Number: 5,767,260
[45] Date of Patent: Jun. 16, 1998

[54] ANTIGEN-BINDING FUSION PROTEINS

[75] Inventors: Marc Whitlow, El Sabrante, Calif.; David Filpula, Piscataway; Robert Shorr, Edison, both of N.J.

[73] Assignee: Enzon Inc., Piscataway, N.J.

[21] Appl. No.: 515,903

[22] Filed: Aug. 16, 1995

Related U.S. Application Data

[62] Division of Ser. No. 323,445, Oct. 13, 1994.

[51] Int. Cl.$^6$ .......................... C12N 15/13; C07H 21/04; C07K 19/00
[52] U.S. Cl. ................. 536/23.4; 536/23.53; 435/240.2; 435/320.1; 435/69.7; 435/252.3; 530/387.3
[58] Field of Search .......................... 536/23.53, 23.4; 530/387.3; 435/240.2, 320.1, 69.7, 252.3

[56] References Cited

U.S. PATENT DOCUMENTS

| | | | |
|---|---|---|---|
| 4,861,581 | 8/1989 | Epstein et al. | 424/1.1 |
| 4,908,773 | 3/1990 | Pantoliano et al. | 364/496 |
| 4,946,778 | 8/1990 | Ladner et al. | 435/69.6 |
| 5,019,368 | 5/1991 | Epstein et al. | 424/1.1 |
| 5,091,513 | 2/1992 | Huston et al. | 530/387 |
| 5,132,405 | 7/1992 | Huston et al. | 530/387.3 |
| 5,258,498 | 11/1993 | Huston et al. | 530/350 |
| 5,260,203 | 11/1993 | Ladner et al. | 435/172.3 |
| 5,476,786 | 12/1995 | Huston | 435/252.33 |

FOREIGN PATENT DOCUMENTS

WO 88/09344  12/1988  WIPO.
WO 93/16185   8/1993  WIPO.

OTHER PUBLICATIONS

Milenic et al., Canc. Res., 1991, 51:616.
Aderem et al., "Evidence for Sequential Signals in the Induction of the Arachidonic Acid Cascade in Macrophages," *J. Exp. Med.* 163:139–154 (Jan. 1986).
Bell et al., "Diglyceride lipase: A pathway for arachidonate release from human platelets," *Proc. Natl. Acad. Sci. USA* 76:3238–3241 (Jul. 1979).
Bollon et al., "Human Cytokines, Tumor Necrosis Factor, and Interferons: Gene Cloning, Animal Studies, and Clinical Trials," *J. Cell. Biochem.* 36:353–367 (1988).
Bomalaski et al., "Identification and isolation of a phospholipase $A_2$, activating protein in human rheumatoid arthritis synovial fluid: Induction of eicosanoid synthesis and an inflammatory response in joints injected in vivo," *J. Lab. Clin. Med.* 116:814–925 (Dec. 1990).
Bomalaski et al., "A Phospholipase $A_2$–Activating Protein (PLAP) Stimulates Human Neutrophil Aggregation and Release of Lysosomal Enzymes, Superoxide, and Eicosanoids," *J. Immunol.* 142:3957–3962 (Jun. 1, 1989).
Bomalaski et al., "Human Extracellular Recombinant Phospholipase $A_2$ Induces an Inflammatory Response in Rabbit Joints," *J. Immunol.* 146:3904–3910 (Jun. 1, 1991).
Bonta & Ben–Efraim, "Involvement of inflammatory mediators in macrophage antitumor activity," *J. Leukocyte Biol.* 54:613–626 (Dec. 1993).

Burch et al., "Phospholipase $A_2$ and phospholipase C are activated by distinct GTP–binding proteins in response to $r_1$–adrenergic stimulation in FRTL5 thyroid cells," *Proc. Natl. Acad. Sci. USA* 83:7201–7205 (Oct. 1986).
Burch & Axelrod, "Dissociation of braykinin–induced prostaglandin formation from phosphatidylinositol turnover in Swiss 3T3 fibroblasts: Evidence for G protein regulation of phospholipase $A_2$," *Proc. Natl. Acad. Sci. USA* 84:6374–6378 (Sep. 1987).
Chau & Tai, "Release of Arachidonate from Diglyceride in Human Platelets Requires the Sequential Action of a Diglyceride Lipase and a Monoglyceride Lipase," *Biochem. Biophys. Res. Commun.* 100:1688–1695 (Jun. 30, 1981).
Clark et al., "The Binding of Leukotriene $C_4$ and Leukotriene $D_4$ to Membranes of a Smooth Muscle Cell Line ($BC3H_1$) and Evidence that Leukotriene Induced Contraction in these cells is mediated by Thromboxane, Protein and RNA Syntheses," *Eur. J. Pharmacol.* 116:207–220 (1985).
Clark et al., "Effect of Leukotrienes, Bradykinin and Calcium Ionophore (A 23187) on Bovine Endothelial Cells: Release of Prostacyclin," *Prostaglandins* 31:157–166 (Jan. 1986).
Clark et al., "Leukotriene $D_4$ Treatment of Bovine Aortic Endothelial Cells and Murine Smooth Muscle Cells in Culture Results in an Increase in Phospholipase $A_2$ Activity," *J. Biol. Chem.* 261:10713–10718 (Aug. 15, 1986).
Clark et al., "Identification and Isolation of a Mammalian Protein Which Is Antigenically and Functionally Related to the Phospholipase $A_2$ Stimulatory Peptide Melittin," *J. Biol. Chem.* 262:4402–4406 (Mar. 25, 1987).
Clark et al., "Tumour necrosis factor (cachectin) induces phospholipae $A_2$ activity and synthesis of a phospholipase $A_2$–activating protein in endothelial cells," *Biochem. J.* 250:125–132 (1988).
Clark et al., "The Role of Phospholipase $A_2$ Activating Protein (PLAP) in Regulating Prostanoid Production in Smooth Muscle and Endothelial Cells following Leukotriene $D_4$ Treatment," *Phospholipase A2:125–144* (1990).
Clark et al., "Cloning of a phospholipase $A_2$–activating protein," *Proc. Natl. Acad. Sci. USA* 88:5418–5422 (Jun. 1991).
Corvalan et al., "Tumour Therapy with Vinca Alkaloids Targeted by a Hybrid–Hybrid Monoclonal Antibody Recognising both Cea and Vinca Alkaloids," *Int. J. Cancer* 2:22–25 (1988).

(List continued on next page.)

*Primary Examiner*—Frank C. Eisenschenk

[57] ABSTRACT

Compositions of, genetic constructions coding for, and methods for producing single-chain and multivalent immunoeffector antigen-binding fusion proteins are provided by the invention. Antigen-binding fusion proteins having phospholipase A activating protein and/or tumor necrosis factor fragments are also provided by the invention. Genetic sequences coding for single-chain and multivalent immunoeffector antigen-binding fusion proteins are disclosed.

8 Claims, 14 Drawing Sheets

OTHER PUBLICATIONS

Dorai et al., "Mammalian Cell Expression of Single–Chain Fv (sFv) Antibody Proteins and Their C–terminal Fusions with Interleukin–2 and Other Effector Domains," *Bio/Technology* 12:890–897 (Sep. 1994).

Dunn et al., "Cloning and Expression of Antibody Fragments for Construction of a Recombinant Immunotoxin," *J. Cellular Biochem.* 18D:Abstract T 512 (Feb. 26–Apr. 17, 1994).

Eck & Sprang, "The Structure of Tumor Necrosis Factor–r at 2.6 A Resolution: Implications for Receptor Binding," *J. Biol. Chem.* 264:17595–17605 (Oct. 15, 1989).

Gillies et al., "Antibody–targeted interleukin 2 stimulates T–cell killing of autologous tumor cells," *Proc. Natl. Acad. Sci. USA* 89:1428–1432 (Feb. 1992).

Gillies et al., "Biological Activity and in Vivo Clearance of Antitumor Antibody/Cytokine Fusion Proteins," *Bioconj. Chem.* 4:230–235 (1993).

Honda et al., "A human hybrid hybridoma producing a bispecific monoclonal antibody that can target tumor cells for attack by *Pseudomonas aeruginosa* exotoxin A," *Cytotechnology* 4:59–68 (1990).

Kolls et al., "Recombinant Cytokines and Pulmonary Host Defense," *Am. J. Med. Sci.* 306:330–335 (Nov. 1993).

LeBarthon et al., *Canc. Res.* 51:2694–2698 (1991).

Loetscher et al., "Human Tumor Necrosis Factor r(TNFr) Mutants with Exclusive Specificity for the 55–kDa or 75–kDa TNF Receptors," *J. Biol. Chem.* 268:26350–26357 (Dec. 15, 1993).

Marmenout et al., "Molecular cloning and expression of human tumor necrosis factor and comparison with mouse tumor necrosis factor," *Eur. J. Biochem.* 152:515–522 (1985).

Muraro et al., "Generation and Characterization of B72.3 Second Generation Monoclonal Antibodies Reactive with the Tumor–associated Glycoprotein 72 Antigen," *Can. Res.* 48:4588–4596 (Aug. 15, 1988).

Pimm et al., "A bispecific monoclonal antibody against methotrexate and a human tumour associated antigen augments cytotoxicity of methotrexate–carrier conjugate," *Brit. J. Can.* 61:508–513 (1990).

Raso & Griffin, "Hybrid Antibodies with Dual Specificity for the Delivery of Ricin to Immunoglobulin–bearing Target Cells," *Cancer Res.* 41:2073–2078 (Jun. 1981).

Savage, Phillip, "Fusion Antibodies with Interleukin for Immune Stimulation," *The Third Annual IBC International Conference on Antibody Engineering: New Technology & Application Implications,* San Diego Marriott Hotel and Marina, Dec. 14–16, 1992.

Savage et al., "A recombinant single chain antibody interleukin–2 fusion protein," *Br. J. Cancer* 67:304–310 (1993).

Staerz et al., "Hybrid antibodies can target sites for attack by T cells," *Nature* 314:628–631 (Apr. 18, 1985).

Songsivilai et al., "Bispecific antibody: a tool for diagnosis and treatment of disease," *Clin. Exp. Immunol.* 79:315–321 (1990).

Van den Bosch, H., "Intracellular Phospholipases A," *Biochem. Biophys. Acta* 604:191–246 (1980).

Vassalli, Pierre, "The Pathophysiology of Tumor Necrosis Factors," *Annu. Rev. Immunol.* 10:411–452 (1992).

Wang et al., "Molecular Cloning of the Complementary DNA for Human Tumor Necrosis Factor," *Science* 228:149–154 (Apr. 12, 1985).

Wozencraft et al., "Killing of Human Malaria Parasites by Macrophage Secretory Products," *Infect. & Immun.* 43:664–669 (Feb. 1984).

Xiang et al., "Recombinant Bifunctional Molecule FV/IFN–v Possesses the Anti–Tumor FV as Well as the Gamma Interferon Activities," *Cancer Biotherapy* 8:327–337 (1993).

CC49 V_L

| | | | | | | 10 | | | | | | | | 20 | |
|---|---|---|---|---|---|---|---|---|---|---|---|---|---|---|---|

Asp Val Val Met Ser Gln Ser Pro Ser Ser Leu Pro Val Ser Val Gly Glu Lys Val Thr
GAC GTC GTG ATG TCA CAG TCT CCA TCC TCC CTA CCT GTG TCA GTT GGC GAG AAG GTT ACT
<ins>Aat II</ins>

30                                        40

Leu Ser Cys Lys Ser Ser Gln Ser Leu Leu Tyr Ser Gln Asn Gln Lys Asn Tyr Leu Ala
TTG AGC TGC AAG TCC AGT CAG AGC CTT TTA TAT AGT GGT AAT CAA AAG AAC TAC TTG GCC 50                                        60

Trp Tyr Gln Gln Lys Pro Gly Gln Ser Pro Lys Leu Leu Ile Tyr Trp Ala Ser Ala Arg
TGG TAC CAG CAG AAA CCA GGG CAG TCT CCT AAA CTG CTG ATT TAC TGG GCA TCC GCT AGG 70                                        80

Glu Ser Gly Val Pro Asp Arg Phe Thr Gly Ser Gly Ser Gly Thr Asp Phe Thr Leu Ser
GAA TCT GGG GTC CCT GAT CGC TTC ACA GGC AGT GGA TCT GGG ACA GAT TTC ACT CTC TCC 90                                        100

Ile Ser Ser Val Lys Thr Glu Asp Leu Ala Val Tyr Tyr Cys Gln Gln Tyr Tyr Ser Tyr
ATC AGC AGT GTG AAG ACT GAA GAC CTG GCA GTT TAT TAC TGT CAG CAG TAT TAT AGC TAT 110              212 Linker      120

Pro Leu Thr Phe Gly Ala Gly Thr Lys Leu Val Leu Lys <ins>Gly Ser Thr Ser Gly Ser Gly</ins>
CCC CTC ACG TTC GGT GCT GGG ACC <ins>AAG CTT</ins> GTG CTG AAA GGC TCT ACT TCC GGT AGC GGC
                                         HindIII

CC49 VH                      140

<ins>Lys Ser Ser Glu Gly Lys Gly</ins> Gln Val Gln Leu Gln Gln Ser Asp Ala Glu Leu Val Lys
<ins>AAA TCC TCT GAA GGC AAA GGT</ins> CAG GTT <ins>CAG CTG CAG</ins> CAG TCT GAC GCT GAG TTG GTG AAA
                                       PvuII PstI 150                                        160

Pro Gly Ala Ser Val Lys Ile Ser Cys Lys Ala Ser Gly Tyr Thr Phe Thr Asp His Ala
CCT GGG GCT TCA GTG AAG ATT TCC TGC AAG GCT TCT GGC TAC ACC TTC ACT GAC CAT GCA 170                                        180

Ile His Trp Val Lys Gln Asn Pro Glu Gln Gly Leu Glu Trp Ile Gly Tyr Phe Ser Pro
ATT CAC TGG GTG AAA CAG AAC CCT GAA CAG GGC CTG GAA TGG ATT GGA TAT TTT TCT CCC 190                                        200

Gly Asn Asp Asp Phe Lys Tyr Asn Glu Arg Phe Lys Gly Lys Ala Thr Leu Thr Ala Asp
GGA AAT GAT GAT TTT AAA TAC AAT GAG AGG TTC AAG GGC AAG GCC ACA CTG ACT GCA GAC

FIG.4A

```
                              210                                              220
Lys Ser Ser Ser Thr Ala Tyr Val Gln Leu Asn Ser Leu Thr Ser Glu Asp Ser Ala Val
AAA TCC TCC AGC ACT GCC TAC GTG CAG CTC AAC AGC CTG ACA TCT GAG GAT TCT GCA GTG 230                                              240
Tyr Phe Cys Thr Arg Ser Leu Asn Met Ala Tyr Trp Gly Gln Gly Thr Ser Val Thr Val
TAT TTC TGT ACA AGA TCC CTG AAT ATG GCC TAC TGG GGT CAA GGA ACC TCG GTC ACC GTC
                                                                    Bst EII
     PLAP                     250                                              260
Ser Glu Ser Pro Leu Ile Ala Lys Val Leu Thr Thr Glu Pro Pro Ile Ile Thr Pro Val
TCC GAA TCT CCG CTG ATC GCT AAA GTT CTG ACT ACC GAA CCA CCT ATT ATC ACT CCG GTT

Arg Arg *** *** Bam HI
CGT CGT TAA TAG GAT CC
```

FIG.4B

```
CC49 V_L                          10                          20
Asp Val Val Met Ser Gln Ser Pro Ser Ser Leu Pro Val Ser Val Gly Glu Lys Val Thr
GAC GTC GTG ATG TCA CAG TCT CCA TCC TCC CTA CCT GTG TCA GTT GGC GAG AAG GTT ACT
Aat II
                                  30                          40
Leu Ser Cys Lys Ser Ser Gln Ser Leu Leu Tyr Ser Gly Asn Gln Lys Asn Tyr Leu Ala
TTG AGC TGC AAG TCC AGT CAG AGC CTT TTA TAT AGT GGT AAT CAA AAG AAC TAC TTG GCC 50                          60
Trp Tyr Gln Gln Lys Pro Gly Gln Ser Pro Lys Leu Leu Ile Tyr Trp Ala Ser Ala Arg
TGG TAC CAG CAG AAA CCA GGG CAG TCT CCT AAA CTG CTG ATT TAC TGG GCA TCC GCT AGG 70                          80
Glu Ser Gly Val Pro Asp Arg Phe Thr Gly Ser Gly Ser Gly Thr Asp Phe Thr Leu Ser
GAA TCT GGG GTC CCT GAT CGC TTC ACA GGC AGT GGA TCT GGG ACA GAT TTC ACT CTC TCC 90                          100
Ile Ser Ser Val Lys Thr Glu Asp Leu Ala Val Tyr Tyr Cys Gln Gln Tyr Tyr Ser Tyr
ATC AGC AGT GTG AAG ACT GAA GAC CTG GCA GTT TAT TAC TGT CAG CAG TAT TAT AGC TAT

110       PLAP Linker       120
Pro Leu Thr Phe Gly Ala Gly Thr Lys Leu Val Leu Lys Glu Ser Pro Leu Ile Ala Lys
CCC CTC ACG TTC GGT GCT GGG ACC AAG CTT GTG CTG AAA GAA TCT CCG CTG ATC GCT AAA
                                      HindIII
                                            CC49 V_H          140
Val Leu Thr Thr Glu Pro Pro Ile Ile Thr Pro Val Arg Arg Gln Val Gln Leu Gln Gln
GTT CTG ACT ACC GAA CCA CCT ATT ATC ACT CCG GTT CGT CGT CAG GTT CAG CTG CAG CAG
                                                              Pvu II Pst I
                                  150                         160
Ser Asp Ala Glu Leu Val Lys Pro Gly Ala Ser Val Lys Ile Ser Cys Lys Ala Ser Gly
TCT GAC GCT GAG TTG GTG AAA CCT GGG GCT TCA GTG AAG ATT TCC TGC AAG GCT TCT GGC 170                         180
Tyr Thr Phe Thr Asp His Ala Ile His Trp Val Lys Gln Asn Pro Glu Gln Gly Leu Glu
TAC ACC TTC ACT GAC CAT GCA ATT CAC TGG GTG AAA CAG AAC CCT GAA CAG GGC CTG GAA 190                         200
Trp Ile Gly Tyr Phe Ser Pro Gly Asn Asp Asp Phe Lys Tyr Asn Glu Arg Phe Lys Gly
TGG ATT GGA TAT TTT TCT CCC GGA AAT GAT GAT TTT AAA TAC AAT GAG AGG TTC AAG GGC
```

FIG.5A

```
                                    210                                          220
     Lys Ala Thr Leu Thr Ala Asp Lys Ser Ser Ser Thr Ala Tyr Val Gln Leu Asn Ser Leu
     AAG GCC ACA CTG ACT GCA GAC AAA TCC TCC AGC ACT GCC TAC GTG CAG CTC AAC AGC CTG 230                                          240
     Thr Ser Glu Asp Ser Ala Val Tyr Phe Cys Thr Arg Ser Leu Asn Met Ala Tyr Trp Gly
     ACA TCT GAG GAT TCT GCA GTG TAT TTC TGT ACA AGA TCC CTG AAT ATG GCC TAC TGG GGT

Gln Gly Thr Ser Val Thr Val Ser *** ***  BamHI
     CAA GGA ACC TCG GTC ACC GTC TCC TAA  TAG GAT CC
                 Bst EII
```

FIG.5B

PLAP
Asp Val Glu Ser Pro Leu Ile Ala Lys Val Leu Thr Thr Glu Pro Pro Ile Ile Thr Pro Val Arg Arg
GAC GTC GAA TCT CCG CTG ATC GCT AAA GTT CTG ACT ACC GAA CCA CCT ATT ATC ACT CCG GTT CGT CGT
Aat II

CC49 V$_L$                                          10                                              20
Asp Val Val Met Ser Gln Ser Pro Ser Ser Leu Pro Val Ser Val Gly Glu Lys Val Thr
GAC GTC GTG ATG TCA CAG TCT CCA TCC TCC CTA CCT GTG TCA GTT GGC GAG AAG GTT ACT
Aat II 30                                              40
Leu Ser Cys Lys Ser Ser Gln Ser Leu Leu Tyr Ser Gly Asn Gln Lys Asn Tyr Leu Ala
TTG AGC TGC AAG TCC AGT CAG AGC CTT TTA TAT AGT GGT AAT CAA AAG AAC TAC TTG GCC 50                                              60
Trp Tyr Gln Gln Lys Pro Gly Gln Ser Pro Lys Leu Leu Ile Tyr Trp Ala Ser Ala Arg
TGG TAC CAG CAG AAA CCA GGG CAG TCT CCT AAA CTG CTG ATT TAC TGG GCA TCC GCT AGG 70                                              80
Glu Ser Gly Val Pro Asp Arg Phe Thr Gly Ser Gly Ser Gly Thr Asp Phe Thr Leu Ser
GAA TCT GGG GTC CCT GAT CGC TTC ACA GGC AGT GGA TCT GGG ACA GAT TTC ACT CTC TCC 90                                              100
Ile Ser Ser Val Lys Thr Glu Asp Leu Ala Val Tyr Tyr Cys Gln Gln Tyr Tyr Ser Tyr
ATC AGC AGT GTG AAG ACT GAA GAC CTG GCA GTT TAT TAC TGT CAG CAG TAT TAT AGC TAT 110            212 Linker                            120
Pro Leu Thr Phe Gly Ala Gly Thr Lys Leu Val Leu Lys Gly Ser Thr Ser Gly Ser Gly
CCC CTC ACG TTC GGT GCT GGG ACC AAG CTT GTG CTG AAA GGC TCT ACT TCC GGT AGC GGC
                                        Hind III CC49 V$_H$                                                                  140
Lys Ser Ser Glu Gly Lys Gly Gln Val Gln Leu Gln Gln Ser Asp Ala Glu Leu Val Lys
AAA TCC TCT GAA GGC AAA GGT CAG GTT CAG CTG CAG CAG TCT GAC GCT GAG TTG GTG AAA
                                        Pvu II Pst I
                                   150                                                  160
Pro Gly Ala Ser Val Lys Ile Ser Cys Lys Ala Ser Gly Tyr Thr Phe Thr Asp His Ala
CCT GGG GCT TCA GTG AAG ATT TCC TGC AAG GCT TCT GGC TAC ACC TTC ACT GAC CAT GCA

FIG.6A

```
                                170                                    180
     Ile His Trp Val Lys Gln Asn Pro Glu Gln Gly Leu Glu Trp Ile Gly Tyr Phe Ser Pro
     ATT CAC TGG GTG AAA CAG AAC CCT GAA CAG GGC CTG GAA TGG ATT GGA TAT TTT TCT CCC 190                                    200
     Gly Asn Asp Asp Phe Lys Tyr Asn Glu Arg Phe Lys Gly Lys Ala Thr Leu Thr Ala Asp
     GGA AAT GAT GAT TTT AAA TAC AAT GAG AGG TTC AAG GGC AAG GCC ACA CTG ACT GCA GAC 210                                    220
     Lys Ser Ser Ser Thr Ala Tyr Val Gln Leu Asn Ser Leu Thr Ser Glu Asp Ser Ala Val
     AAA TCC TCC AGC ACT GCC TAC GTG CAG CTC AAC AGC CTG ACA TCT GAG GAT TCT GCA GTG 230                                    240
     Tyr Phe Cys Thr Arg Ser Leu Asn Met Ala Tyr Trp Gly Gln Gly Thr Ser Val Thr Val
     TAT TTC TGT ACA AGA TCC CTG AAT ATG GCC TAC TGG GGT CAA GGA ACC TCA GTC ACC GTC

Ser *** *** Bam H1
     TCC TAA TAG GAT CC
```

FIG.6B

```
CACACCCTGA CAAGCTGCCA GGCAGGTTCT CTTCCTCTCA CATACTGACC CACGGCTCCA    60

CCCTCTCTCC CCTGGAAAGG ACACC ATG AGC ACT GAA AGC ATG ATC CGG GAC     112
                           Met Ser Thr Glu Ser Met Ile Arg Asp
                            1               5

GTG GAG CTG GCC GAG GAG GCG CTC CCC AAG AAG ACA GGG GGG CCC CAG     160
Val Glu Leu Ala Glu Glu Ala Leu Pro Lys Lys Thr Gly Gly Pro Gln
 10              15              20              25

GGC TCC AGG CGG TGC TTG TTC CTC AGC CTC TTC TCC TTC CTG ATC GTG     208
Gly Ser Arg Arg Cys Leu Phe Leu Ser Leu Phe Ser Phe Leu Ile Val
              30              35              40

GCA GGC GCC ACC ACG CTC TTC TGC CTG CTG CAC TTT GGA GTG ATC GGC     256
Ala Gly Ala Thr Thr Leu Phe Cys Leu Leu His Phe Gly Val Ile Gly
              45              50              55

CCC CAG AGG GAA GAG TCC CCC AGG GAC CTC TCT CTA ATC AGC CCT CTG     304
Pro Gln Arg Glu Glu Ser Pro Arg Asp Leu Ser Leu Ile Ser Pro Leu
             60              65              70

GCC CAG GCA GTC AGA TCA TCT TCT CGA ACC CCG AGT GAC AAG CCT GTA     352
Ala Gln Ala Val Arg Ser Ser Ser Arg Thr Pro Ser Asp Lys Pro Val
         75          80              85

GCC CAT GTT GTA GCA AAC CCT CAA GCT GAG GGG CAG CTC CAG TGG CTG     400
Ala His Val Val Ala Asn Pro Gln Ala Glu Gly Gln Leu Gln Trp Leu
 90              95              100             105

AAC CGC CGG GCC AAT GCC CTC CTG GCC AAT GGC GTG GAG CTG AGA GAT     448
Asn Arg Arg Ala Asn Ala Leu Leu Ala Asn Gly Val Glu Leu Arg Asp
              110             115             120

AAC CAC CTG GTG GTG CCA TCA GAG GGC CTG TAC CTC ATC TAC TCC CAG     496
Asn His Leu Val Val Pro Ser Glu Gly Leu Tyr Leu Ile Tyr Ser Gln
             125             130             135
```

FIG.8A

```
GTC CTC TTC AAG GGC CAA GGC TGC CCC TCC ACC CAT GTG CTC CTC ACC         544
Val Leu Phe Lys Gly Gln Gly Cys Pro Ser Thr His Val Leu Leu Thr
        140                 145                 150

CAC ACC ATC AGC CGC ATC GCC GTC TCC TAC CAG ACC AAG GTC AAC CTC         592
His Thr Ile Ser Arg Ile Ala Val Ser Tyr Gln Thr Lys Val Asn Leu
        155                 160                 165

CTC TCT GCC ATC AAG AGC CCC TGC CAG AGG GAG ACC CCA GAG GGG GCT         640
Leu Ser Ala Ile Lys Ser Pro Cys Gln Arg Glu Thr Pro Glu Gly Ala
170                 175                 180                 185

GAG GCC AAG CCC TGG TAT GAG CCC ATC TAT CTG GGA GGG GTC TTC CAG         688
Glu Ala Lys Pro Trp Tyr Glu Pro Ile Tyr Leu Gly Gly Val Phe Gln
                190                 195                 200

CTG GAG AAG GGT GAC CGA CTC AGC GCT GAG ATC AAT CGG CCC GAC TAT         736
Leu Glu Lys Gly Asp Arg Leu Ser Ala Glu Ile Asn Arg Pro Asp Tyr
        205                 210                 215

CTC GAC TTT GCC GAG TCT GGG CAG GTC TAC TTT GGG ATC ATT GCC CTG         784
Leu Asp Phe Ala Glu Ser Gly Gln Val Tyr Phe Gly Ile Ile Ala Leu
        220                 225                 230

TGAGGAGGAC GAACATCCAA CCTTCCCAAA CGCCTCCCCT GCCCCAATCC CTTTATTACC      844

CCCTCCTTCA GACACCCTCA ACCTCTTCTG GCTCAAAAAG AGAATTGGGG GCTTAG          900
```

FIG.8B

CC49 V_H sFv                                    240                      245
- Asn Met Ala Tyr Trp Gly Gln Gly Thr Ser Val Thr Val Ser * *
- AAT ATG GCC TAC TGG GGT CAA GGA ACC TCA GTC ACC GTC TCC TAA TAG GAT CC
                                                                    Bam HI

TNF         1                     10
     NH_2 - Met Val | Arg Ser Ser Ser Arg Thr Pro Ser Asp - to COOH TERMINUS |
     DELETE ◄──┘            └────────────────────────────────────┐
                                                                 ▼
CC49 V_H sFv                                    240                      245      INSERT TNF
- Asn Met Ala Tyr Trp Gly Gln Gly Thr Ser Val Thr Val Ser Gly Ser Arg Ser
                                                              Spacer
250                      255
Ser Ser Arg Thr Pro Ser Asp -

FIG.9A

CC49 V_H sFv                                    240                      245
- Asn Met Ala Tyr Trp Gly Gln Gly Thr Ser Val Thr Val Ser Gly Ser Gly Lys
                                                              Spacer
250                      255 TNF             260
Pro Gly Ser Gly Glu Gly Arg Ser Ser Ser Arg Thr Pro Ser Asp -

FIG.9B

CC49 V_H sFv                          240                    245
 - Asn Met Ala Tyr Trp Gly Gln Gly Thr Ser Val Thr Val Ser Gly Ser His His
                                                               ―――――――――――
                                                                  Spacer
250                    TNF           260
His His His Ser Gly Arg Ser Ser Ser Arg Thr Pro Ser Asp -
―――――――――――――――

CC49 VH          | His_5 Spacer              | PLAP
Val Thr Val Ser Gly Ser His His His His His Ser Gly Glu Ser Pro Leu..

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: both ( x i ) SEQUENCE DESCRIPTION: SEQ ID NO:1:

```
Glu  Ser  Pro  Leu  Ile  Ala  Lys  Val  Leu  Thr  Thr  Glu  Pro  Pro  Ile  Ile
 1              5                         10                        15

Thr  Pro  Val  Arg  Arg
              20
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: both ( x i ) SEQUENCE DESCRIPTION: SEQ ID NO:2:

```
Gly  Ser  His  His  His  His  His  Ser  Gly
 1              5
```

( 2 ) INFORMATION FOR SEQ ID NO:3:

( i ) SEQUENCE CHARACTERISTICS:
        ( A ) LENGTH: 797 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: 1..786

( x i ) SEQUENCE DESCRIPTION: SEQ ID NO:3:

```
GAC  GTC  GTG  ATG  TCA  CAG  TCT  CCA  TCC  TCC  CTA  CCT  GTG  TCA  GTT  GGC     48
Asp  Val  Val  Met  Ser  Gln  Ser  Pro  Ser  Ser  Leu  Pro  Val  Ser  Val  Gly
 1              5                         10                        15

GAG  AAG  GTT  ACT  TTG  AGC  TGC  AAG  TCC  AGT  CAG  AGC  CTT  TTA  TAT  AGT     96
Glu  Lys  Val  Thr  Leu  Ser  Cys  Lys  Ser  Ser  Gln  Ser  Leu  Leu  Tyr  Ser
                20                        25                        30

GGT  AAT  CAA  AAG  AAC  TAC  TTG  GCC  TGG  TAC  CAG  CAG  AAA  CCA  GGG  CAG    144
Gly  Asn  Gln  Lys  Asn  Tyr  Leu  Ala  Trp  Tyr  Gln  Gln  Lys  Pro  Gly  Gln
           35                        40                        45

TCT  CCT  AAA  CTG  CTG  ATT  TAC  TGG  GCA  TCC  GCT  AGG  GAA  TCT  GGG  GTC    192
Ser  Pro  Lys  Leu  Leu  Ile  Tyr  Trp  Ala  Ser  Ala  Arg  Glu  Ser  Gly  Val
      50                        55                        60

CCT  GAT  CGC  TTC  ACA  GGC  AGT  GGA  TCT  GGG  ACA  GAT  TTC  ACT  CTC  TCC    240
Pro  Asp  Arg  Phe  Thr  Gly  Ser  Gly  Ser  Gly  Thr  Asp  Phe  Thr  Leu  Ser
 65                        70                        75                  80

ATC  AGC  AGT  GTG  AAG  ACT  GAA  GAC  CTG  GCA  GTT  TAT  TAC  TGT  CAG  CAG    288
Ile  Ser  Ser  Val  Lys  Thr  Glu  Asp  Leu  Ala  Val  Tyr  Tyr  Cys  Gln  Gln
                85                        90                        95

TAT  TAT  AGC  TAT  CCC  CTC  ACG  TTC  GGT  GCT  GGG  ACC  AAG  CTT  GTG  CTG    336
Tyr  Tyr  Ser  Tyr  Pro  Leu  Thr  Phe  Gly  Ala  Gly  Thr  Lys  Leu  Val  Leu
           100                       105                       110

AAA  GGC  TCT  ACT  TCC  GGT  AGC  GGC  AAA  TCC  TCT  GAA  GGC  AAA  GGT  CAG    384
Lys  Gly  Ser  Thr  Ser  Gly  Ser  Gly  Lys  Ser  Ser  Glu  Gly  Lys  Gly  Gln
      115                       120                       125

GTT  CAG  CTG  CAG  CAG  TCT  GAC  GCT  GAG  TTG  GTG  AAA  CCT  GGG  GCT  TCA    432
Val  Gln  Leu  Gln  Gln  Ser  Asp  Ala  Glu  Leu  Val  Lys  Pro  Gly  Ala  Ser
 130                       135                       140
```

| | | | | | | | | | | | | | | | | |
|---|---|---|---|---|---|---|---|---|---|---|---|---|---|---|---|---|
| GTG | AAG | ATT | TCC | TGC | AAG | GCT | TCT | GGC | TAC | ACC | TTC | ACT | GAC | CAT | GCA | 480 |
| Val | Lys | Ile | Ser | Cys | Lys | Ala | Ser | Gly | Tyr | Thr | Phe | Thr | Asp | His | Ala | |
| 145 | | | | 150 | | | | | 155 | | | | | | 160 | |
| ATT | CAC | TGG | GTG | AAA | CAG | AAC | CCT | GAA | CAG | GGC | CTG | GAA | TGG | ATT | GGA | 528 |
| Ile | His | Trp | Val | Lys | Gln | Asn | Pro | Glu | Gln | Gly | Leu | Glu | Trp | Ile | Gly | |
| | | | | 165 | | | | | 170 | | | | | 175 | | |
| TAT | TTT | TCT | CCC | GGA | AAT | GAT | GAT | TTT | AAA | TAC | AAT | GAG | AGG | TTC | AAG | 576 |
| Tyr | Phe | Ser | Pro | Gly | Asn | Asp | Asp | Phe | Lys | Tyr | Asn | Glu | Arg | Phe | Lys | |
| | | | 180 | | | | | 185 | | | | | 190 | | | |
| GGC | AAG | GCC | ACA | CTG | ACT | GCA | GAC | AAA | TCC | TCC | AGC | ACT | GCC | TAC | GTG | 624 |
| Gly | Lys | Ala | Thr | Leu | Thr | Ala | Asp | Lys | Ser | Ser | Ser | Thr | Ala | Tyr | Val | |
| | | 195 | | | | 200 | | | | | 205 | | | | | |
| CAG | CTC | AAC | AGC | CTG | ACA | TCT | GAG | GAT | TCT | GCA | GTG | TAT | TTC | TGT | ACA | 672 |
| Gln | Leu | Asn | Ser | Leu | Thr | Ser | Glu | Asp | Ser | Ala | Val | Tyr | Phe | Cys | Thr | |
| | 210 | | | | | 215 | | | | | 220 | | | | | |
| AGA | TCC | CTG | AAT | ATG | GCC | TAC | TGG | GGT | CAA | GGA | ACC | TCG | GTC | ACC | GTC | 720 |
| Arg | Ser | Leu | Asn | Met | Ala | Tyr | Trp | Gly | Gln | Gly | Thr | Ser | Val | Thr | Val | |
| 225 | | | | | 230 | | | | | 235 | | | | | 240 | |
| TCC | GAA | TCT | CCG | CTG | ATC | GCT | AAA | GTT | CTG | ACT | ACC | GAA | CCA | CCT | ATT | 768 |
| Ser | Glu | Ser | Pro | Leu | Ile | Ala | Lys | Val | Leu | Thr | Thr | Glu | Pro | Pro | Ile | |
| | | | | 245 | | | | | 250 | | | | | 255 | | |
| ATC | ACT | CCG | GTT | CGT | CGT | TAATAGGATC | C | | | | | | | | | 797 |
| Ile | Thr | Pro | Val | Arg | Arg | | | | | | | | | | | |
| | | | 260 | | | | | | | | | | | | | |

( 2 ) INFORMATION FOR SEQ ID NO:4:

( i ) SEQUENCE CHARACTERISTICS:
    ( A ) LENGTH: 262 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Asp | Val | Val | Met | Ser | Gln | Ser | Pro | Ser | Ser | Leu | Pro | Val | Ser | Val | Gly |
| 1 | | | | 5 | | | | | 10 | | | | | 15 | |
| Glu | Lys | Val | Thr | Leu | Ser | Cys | Lys | Ser | Ser | Gln | Ser | Leu | Leu | Tyr | Ser |
| | | | 20 | | | | | 25 | | | | | 30 | | |
| Gly | Asn | Gln | Lys | Asn | Tyr | Leu | Ala | Trp | Tyr | Gln | Gln | Lys | Pro | Gly | Gln |
| | | 35 | | | | | 40 | | | | | 45 | | | |
| Ser | Pro | Lys | Leu | Leu | Ile | Tyr | Trp | Ala | Ser | Ala | Arg | Glu | Ser | Gly | Val |
| | 50 | | | | | 55 | | | | | 60 | | | | |
| Pro | Asp | Arg | Phe | Thr | Gly | Ser | Gly | Ser | Gly | Thr | Asp | Phe | Thr | Leu | Ser |
| 65 | | | | | 70 | | | | | 75 | | | | | 80 |
| Ile | Ser | Ser | Val | Lys | Thr | Glu | Asp | Leu | Ala | Val | Tyr | Tyr | Cys | Gln | Gln |
| | | | | 85 | | | | | 90 | | | | | 95 | |
| Tyr | Tyr | Ser | Tyr | Pro | Leu | Thr | Phe | Gly | Ala | Gly | Thr | Lys | Leu | Val | Leu |
| | | | 100 | | | | | 105 | | | | | 110 | | |
| Lys | Gly | Ser | Thr | Ser | Gly | Ser | Gly | Lys | Ser | Ser | Glu | Gly | Lys | Gly | Gln |
| | | | 115 | | | | | 120 | | | | | 125 | | |
| Val | Gln | Leu | Gln | Gln | Ser | Asp | Ala | Glu | Leu | Val | Lys | Pro | Gly | Ala | Ser |
| | 130 | | | | | 135 | | | | | 140 | | | | |
| Val | Lys | Ile | Ser | Cys | Lys | Ala | Ser | Gly | Tyr | Thr | Phe | Thr | Asp | His | Ala |
| 145 | | | | | 150 | | | | | 155 | | | | | 160 |
| Ile | His | Trp | Val | Lys | Gln | Asn | Pro | Glu | Gln | Gly | Leu | Glu | Trp | Ile | Gly |
| | | | | 165 | | | | | 170 | | | | | 175 | |
| Tyr | Phe | Ser | Pro | Gly | Asn | Asp | Asp | Phe | Lys | Tyr | Asn | Glu | Arg | Phe | Lys |
| | | | 180 | | | | | 185 | | | | | 190 | | |

| | | | | | | | | | | | | | | |
|---|---|---|---|---|---|---|---|---|---|---|---|---|---|---|
|Gly|Lys|Ala|Thr|Leu|Thr|Ala|Asp|Lys|Ser|Ser|Ser|Thr|Ala|Tyr|Val|
| | |195| | | |200| | | |205| | | | |

| | | | | | | | | | | | | | | | |
|---|---|---|---|---|---|---|---|---|---|---|---|---|---|---|---|
|Gln|Leu|Asn|Ser|Leu|Thr|Ser|Glu|Asp|Ser|Ala|Val|Tyr|Phe|Cys|Thr|
| |210| | | |215| | | | |220| | | | | |

| | | | | | | | | | | | | | | | |
|---|---|---|---|---|---|---|---|---|---|---|---|---|---|---|---|
|Arg|Ser|Leu|Asn|Met|Ala|Tyr|Trp|Gly|Gln|Gly|Thr|Ser|Val|Thr|Val|
|225| | | | |230| | | | |235| | | | |240|

| | | | | | | | | | | | | | | | |
|---|---|---|---|---|---|---|---|---|---|---|---|---|---|---|---|
|Ser|Glu|Ser|Pro|Leu|Ile|Ala|Lys|Val|Leu|Thr|Thr|Glu|Pro|Pro|Ile|
| | | | |245| | | | |250| | | | |255| |

| | | | | |
|---|---|---|---|---|
|Ile|Thr|Pro|Val|Arg|Arg|
| | | |260| | |

( 2 ) INFORMATION FOR SEQ ID NO:5:

( i ) SEQUENCE CHARACTERISTICS:
        ( A ) LENGTH: 755 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: 1..744

( x i ) SEQUENCE DESCRIPTION: SEQ ID NO:5:

| | | | | | | | | | | | | | | | | |
|---|---|---|---|---|---|---|---|---|---|---|---|---|---|---|---|---|
|GAC|GTC|GTG|ATG|TCA|CAG|TCT|CCA|TCC|TCC|CTA|CCT|GTG|TCA|GTT|GGC|48|
|Asp|Val|Val|Met|Ser|Gln|Ser|Pro|Ser|Ser|Leu|Pro|Val|Ser|Val|Gly| |
|1| | | |5| | | | |10| | | | |15| | |

| | | | | | | | | | | | | | | | | |
|---|---|---|---|---|---|---|---|---|---|---|---|---|---|---|---|---|
|GAG|AAG|GTT|ACT|TTG|AGC|TGC|AAG|TCC|AGT|CAG|AGC|CTT|TTA|TAT|AGT|96|
|Glu|Lys|Val|Thr|Leu|Ser|Cys|Lys|Ser|Ser|Gln|Ser|Leu|Leu|Tyr|Ser| |
| | | |20| | | | |25| | | | |30| | | |

| | | | | | | | | | | | | | | | | |
|---|---|---|---|---|---|---|---|---|---|---|---|---|---|---|---|---|
|GGT|AAT|CAA|AAG|AAC|TAC|TTG|GCC|TGG|TAC|CAG|CAG|AAA|CCA|GGG|CAG|144|
|Gly|Asn|Gln|Lys|Asn|Tyr|Leu|Ala|Trp|Tyr|Gln|Gln|Lys|Pro|Gly|Gln| |
| | |35| | | | |40| | | | |45| | | | |

| | | | | | | | | | | | | | | | | |
|---|---|---|---|---|---|---|---|---|---|---|---|---|---|---|---|---|
|TCT|CCT|AAA|CTG|CTG|ATT|TAC|TGG|GCA|TCC|GCT|AGG|GAA|TCT|GGG|GTC|192|
|Ser|Pro|Lys|Leu|Leu|Ile|Tyr|Trp|Ala|Ser|Ala|Arg|Glu|Ser|Gly|Val| |
| |50| | | | |55| | | | |60| | | | | |

| | | | | | | | | | | | | | | | | |
|---|---|---|---|---|---|---|---|---|---|---|---|---|---|---|---|---|
|CCT|GAT|CGC|TTC|ACA|GGC|AGT|GGA|TCT|GGG|ACA|GAT|TTC|ACT|CTC|TCC|240|
|Pro|Asp|Arg|Phe|Thr|Gly|Ser|Gly|Ser|Gly|Thr|Asp|Phe|Thr|Leu|Ser| |
|65| | | | |70| | | | |75| | | | |80| |

| | | | | | | | | | | | | | | | | |
|---|---|---|---|---|---|---|---|---|---|---|---|---|---|---|---|---|
|ATC|AGC|AGT|GTG|AAG|ACT|GAA|GAC|CTG|GCA|GTT|TAT|TAC|TGT|CAG|CAG|288|
|Ile|Ser|Ser|Val|Lys|Thr|Glu|Asp|Leu|Ala|Val|Tyr|Tyr|Cys|Gln|Gln| |
| | | | |85| | | | |90| | | | |95| | |

| | | | | | | | | | | | | | | | | |
|---|---|---|---|---|---|---|---|---|---|---|---|---|---|---|---|---|
|TAT|TAT|AGC|TAT|CCC|CTC|ACG|TTC|GGT|GCT|GGG|ACC|AAG|CTT|GTG|CTG|336|
|Tyr|Tyr|Ser|Tyr|Pro|Leu|Thr|Phe|Gly|Ala|Gly|Thr|Lys|Leu|Val|Leu| |
| | | |100| | | | |105| | | | |110| | | |

| | | | | | | | | | | | | | | | | |
|---|---|---|---|---|---|---|---|---|---|---|---|---|---|---|---|---|
|AAA|GAA|TCT|CCG|CTG|ATC|GCT|AAA|GTT|CTG|ACT|ACC|GAA|CCA|CCT|ATT|384|
|Lys|Glu|Ser|Pro|Leu|Ile|Ala|Lys|Val|Leu|Thr|Thr|Glu|Pro|Pro|Ile| |
| | |115| | | | |120| | | | |125| | | | |

| | | | | | | | | | | | | | | | | |
|---|---|---|---|---|---|---|---|---|---|---|---|---|---|---|---|---|
|ATC|ACT|CCG|GTT|CGT|CGT|CAG|GTT|CAG|CTG|CAG|CAG|TCT|GAC|GCT|GAG|432|
|Ile|Thr|Pro|Val|Arg|Arg|Gln|Val|Gln|Leu|Gln|Gln|Ser|Asp|Ala|Glu| |
| |130| | | | |135| | | | |140| | | | | |

| | | | | | | | | | | | | | | | | |
|---|---|---|---|---|---|---|---|---|---|---|---|---|---|---|---|---|
|TTG|GTG|AAA|CCT|GGG|GCT|TCA|GTG|AAG|ATT|TCC|TGC|AAG|GCT|TCT|GGC|480|
|Leu|Val|Lys|Pro|Gly|Ala|Ser|Val|Lys|Ile|Ser|Cys|Lys|Ala|Ser|Gly| |
|145| | | | |150| | | | |155| | | | |160| |

| | | | | | | | | | | | | | | | | |
|---|---|---|---|---|---|---|---|---|---|---|---|---|---|---|---|---|
|TAC|ACC|TTC|ACT|GAC|CAT|GCA|ATT|CAC|TGG|GTG|AAA|CAG|AAC|CCT|GAA|528|
|Tyr|Thr|Phe|Thr|Asp|His|Ala|Ile|His|Trp|Val|Lys|Gln|Asn|Pro|Glu| |
| | | | |165| | | | |170| | | | |175| | |

| | | | | | | | | | | | | | | | | |
|---|---|---|---|---|---|---|---|---|---|---|---|---|---|---|---|---|
|CAG|GGC|CTG|GAA|TGG|ATT|GGA|TAT|TTT|TCT|CCC|GGA|AAT|GAT|GAT|TTT|576|
|Gln|Gly|Leu|Glu|Trp|Ile|Gly|Tyr|Phe|Ser|Pro|Gly|Asn|Asp|Asp|Phe| |
| | | |180| | | | |185| | | | |190| | | |

| | | | | | | | | | | | | | | | | |
|---|---|---|---|---|---|---|---|---|---|---|---|---|---|---|---|---|
|AAA|TAC|AAT|GAG|AGG|TTC|AAG|GGC|AAG|GCC|ACA|CTG|ACT|GCA|GAC|AAA|624|

|     |     |     |     |     |     |     |     |     |     |     |     |     |     |     |     |     |
|---|---|---|---|---|---|---|---|---|---|---|---|---|---|---|---|---|
| Lys | Tyr | Asn 195 | Glu | Arg | Phe | Lys | Gly 200 | Lys | Ala | Thr | Leu | Thr 205 | Ala | Asp | Lys |     |
| TCC | TCC | AGC | ACT | GCC | TAC | GTG | CAG | CTC | AAC | AGC | CTG | ACA | TCT | GAG | GAT | 672 |
| Ser | Ser 210 | Ser | Thr | Ala | Tyr | Val 215 | Gln | Leu | Asn | Ser | Leu 220 | Thr | Ser | Glu | Asp |     |
| TCT | GCA | GTG | TAT | TTC | TGT | ACA | AGA | TCC | CTG | AAT | ATG | GCC | TAC | TGG | GGT | 720 |
| Ser 225 | Ala | Val | Tyr | Phe | Cys 230 | Thr | Arg | Ser | Leu | Asn 235 | Met | Ala | Tyr | Trp | Gly 240 |     |
| CAA | GGA | ACC | TCG | ACC | GTC | TCC | TAATAGGATC | C |  |  |  |  |  |  |  | 755 |
| Gln | Gly | Thr | Ser | Val 245 | Thr | Val | Ser |  |  |  |  |  |  |  |  |     |

( 2 ) INFORMATION FOR SEQ ID NO:6:

( i ) SEQUENCE CHARACTERISTICS:
        ( A ) LENGTH: 248 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

|     |     |     |     |     |     |     |     |     |     |     |     |     |     |     |     |
|---|---|---|---|---|---|---|---|---|---|---|---|---|---|---|---|
| Asp 1 | Val | Val | Met | Ser 5 | Gln | Ser | Pro | Ser | Ser 10 | Leu | Pro | Val | Ser | Val 15 | Gly |
| Glu | Lys | Val | Thr 20 | Leu | Ser | Cys | Lys | Ser 25 | Ser | Gln | Ser | Leu | Leu 30 | Tyr | Ser |
| Gly | Asn | Gln 35 | Lys | Asn | Tyr | Leu | Ala 40 | Trp | Tyr | Gln | Gln | Lys 45 | Pro | Gly | Gln |
| Ser | Pro 50 | Lys | Leu | Leu | Ile | Tyr 55 | Trp | Ala | Ser | Ala | Arg 60 | Glu | Ser | Gly | Val |
| Pro 65 | Asp | Arg | Phe | Thr | Gly 70 | Ser | Gly | Ser | Gly | Thr 75 | Asp | Phe | Thr | Leu | Ser 80 |
| Ile | Ser | Ser | Val | Lys 85 | Thr | Glu | Asp | Leu | Ala 90 | Val | Tyr | Tyr | Cys | Gln 95 | Gln |
| Tyr | Tyr | Ser | Tyr 100 | Pro | Leu | Thr | Phe | Gly 105 | Ala | Gly | Thr | Lys | Leu 110 | Val | Leu |
| Lys | Glu | Ser 115 | Pro | Leu | Ile | Ala | Lys 120 | Val | Leu | Thr | Thr | Glu 125 | Pro | Pro | Ile |
| Ile | Thr 130 | Pro | Val | Arg | Arg | Gln 135 | Val | Leu | Gln | Gln | Ser 140 | Asp | Ala | Glu |  |
| Leu 145 | Val | Lys | Pro | Gly | Ala 150 | Ser | Val | Lys | Ile | Ser 155 | Cys | Lys | Ala | Ser | Gly 160 |
| Tyr | Thr | Phe | Thr | Asp 165 | His | Ala | Ile | His | Trp 170 | Val | Lys | Gln | Asn | Pro 175 | Glu |
| Gln | Gly | Leu | Glu 180 | Trp | Ile | Gly | Tyr | Phe 185 | Ser | Pro | Gly | Asn | Asp 190 | Asp | Phe |
| Lys | Tyr | Asn 195 | Glu | Arg | Phe | Lys | Gly 200 | Lys | Ala | Thr | Leu | Thr 205 | Ala | Asp | Lys |
| Ser | Ser 210 | Ser | Thr | Ala | Tyr | Val 215 | Gln | Leu | Asn | Ser | Leu 220 | Thr | Ser | Glu | Asp |
| Ser 225 | Ala | Val | Tyr | Phe | Cys 230 | Thr | Arg | Ser | Leu | Asn 235 | Met | Ala | Tyr | Trp | Gly 240 |
| Gln | Gly | Thr | Ser | Val 245 | Thr | Val | Ser |  |  |  |  |  |  |  |  |

( 2 ) INFORMATION FOR SEQ ID NO:7:

( i ) SEQUENCE CHARACTERISTICS:
        ( A ) LENGTH: 803 base pairs ( B ) TYPE: nucleic acid
( C ) STRANDEDNESS: both
( D ) TOPOLOGY: both ( i x ) FEATURE:
( A ) NAME/KEY: CDS
( B ) LOCATION: 1..792

( x i ) SEQUENCE DESCRIPTION: SEQ ID NO:7:

| GAC | GTC | GAA | TCT | CCG | CTG | ATC | GCT | AAA | GTT | CTG | ACT | ACC | GAA | CCA | CCT | 48 |
| Asp | Val | Glu | Ser | Pro | Leu | Ile | Ala | Lys | Val | Leu | Thr | Thr | Glu | Pro | Pro | |
| 1 | | | | 5 | | | | | 10 | | | | | 15 | | |

| ATT | ATC | ACT | CCG | GTT | CGT | CGT | GAC | GTC | GTG | ATG | TCA | CAG | TCT | CCA | TCC | 96 |
| Ile | Ile | Thr | Pro | Val | Arg | Arg | Asp | Val | Val | Met | Ser | Gln | Ser | Pro | Ser | |
| | | | 20 | | | | | 25 | | | | | 30 | | | |

| TCC | CTA | CCT | GTG | TCA | GTT | GGC | GAG | AAG | GTT | ACT | TTG | AGC | TGC | AAG | TCC | 144 |
| Ser | Leu | Pro | Val | Ser | Val | Gly | Glu | Lys | Val | Thr | Leu | Ser | Cys | Lys | Ser | |
| | | 35 | | | | | 40 | | | | | 45 | | | | |

| AGT | CAG | AGC | CTT | TTA | TAT | AGT | GGT | AAT | CAA | AAG | AAC | TAC | TTG | GCC | TGG | 192 |
| Ser | Gln | Ser | Leu | Leu | Tyr | Ser | Gly | Asn | Gln | Lys | Asn | Tyr | Leu | Ala | Trp | |
| | 50 | | | | | 55 | | | | | 60 | | | | | |

| TAC | CAG | CAG | AAA | CCA | GGG | CAG | TCT | CCT | AAA | CTG | CTG | ATT | TAC | TGG | GCA | 240 |
| Tyr | Gln | Gln | Lys | Pro | Gly | Gln | Ser | Pro | Lys | Leu | Leu | Ile | Tyr | Trp | Ala | |
| 65 | | | | | 70 | | | | | 75 | | | | | 80 | |

| TCC | GCT | AGG | GAA | TCT | GGG | GTC | CCT | GAT | CGC | TTC | ACA | GGC | AGT | GGA | TCT | 288 |
| Ser | Ala | Arg | Glu | Ser | Gly | Val | Pro | Asp | Arg | Phe | Thr | Gly | Ser | Gly | Ser | |
| | | | | 85 | | | | | 90 | | | | | 95 | | |

| GGG | ACA | GAT | TTC | ACT | CTC | TCC | ATC | AGC | AGT | GTG | AAG | ACT | GAA | GAC | CTG | 336 |
| Gly | Thr | Asp | Phe | Thr | Leu | Ser | Ile | Ser | Ser | Val | Lys | Thr | Glu | Asp | Leu | |
| | | | 100 | | | | | 105 | | | | | 110 | | | |

| GCA | GTT | TAT | TAC | TGT | CAG | CAG | TAT | TAT | AGC | TAT | CCC | CTC | ACG | TTC | GGT | 384 |
| Ala | Val | Tyr | Tyr | Cys | Gln | Gln | Tyr | Tyr | Ser | Tyr | Pro | Leu | Thr | Phe | Gly | |
| | | 115 | | | | | 120 | | | | | 125 | | | | |

| GCT | GGG | ACC | AAG | CTT | GTG | CTG | AAA | GGC | TCT | ACT | TCC | GGT | AGC | GGC | AAA | 432 |
| Ala | Gly | Thr | Lys | Leu | Val | Leu | Lys | Gly | Ser | Thr | Ser | Gly | Ser | Gly | Lys | |
| | 130 | | | | | 135 | | | | | 140 | | | | | |

| TCC | TCT | GAA | GGC | AAA | GGT | CAG | GTT | CAG | CTG | CAG | CAG | TCT | GAC | GCT | GAG | 480 |
| Ser | Ser | Glu | Gly | Lys | Gly | Gln | Val | Gln | Leu | Gln | Gln | Ser | Asp | Ala | Glu | |
| 145 | | | | | 150 | | | | | 155 | | | | | 160 | |

| TTG | GTG | AAA | CCT | GGG | GCT | TCA | GTG | AAG | ATT | TCC | TGC | AAG | GCT | TCT | GGC | 528 |
| Leu | Val | Lys | Pro | Gly | Ala | Ser | Val | Lys | Ile | Ser | Cys | Lys | Ala | Ser | Gly | |
| | | | | 165 | | | | | 170 | | | | | 175 | | |

| TAC | ACC | TTC | ACT | GAC | CAT | GCA | ATT | CAC | TGG | GTG | AAA | CAG | AAC | CCT | GAA | 576 |
| Tyr | Thr | Phe | Thr | Asp | His | Ala | Ile | His | Trp | Val | Lys | Gln | Asn | Pro | Glu | |
| | | | 180 | | | | | 185 | | | | | 190 | | | |

| CAG | GGC | CTG | GAA | TGG | ATT | GGA | TAT | TTT | TCT | CCC | GGA | AAT | GAT | GAT | TTT | 624 |
| Gln | Gly | Leu | Glu | Trp | Ile | Gly | Tyr | Phe | Ser | Pro | Gly | Asn | Asp | Asp | Phe | |
| | | 195 | | | | | 200 | | | | | 205 | | | | |

| AAA | TAC | AAT | GAG | AGG | TTC | AAG | GGC | AAG | GCC | ACA | CTG | ACT | GCA | GAC | AAA | 672 |
| Lys | Tyr | Asn | Glu | Arg | Phe | Lys | Gly | Lys | Ala | Thr | Leu | Thr | Ala | Asp | Lys | |
| | 210 | | | | | 215 | | | | | 220 | | | | | |

| TCC | TCC | AGC | ACT | GCC | TAC | GTG | CAG | CTC | AAC | AGC | CTG | ACA | TCT | GAG | GAT | 720 |
| Ser | Ser | Ser | Thr | Ala | Tyr | Val | Gln | Leu | Asn | Ser | Leu | Thr | Ser | Glu | Asp | |
| 225 | | | | | 230 | | | | | 235 | | | | | 240 | |

| TCT | GCA | GTG | TAT | TTC | TGT | ACA | AGA | TCC | CTG | AAT | ATG | GCC | TAC | TGG | GGT | 768 |
| Ser | Ala | Val | Tyr | Phe | Cys | Thr | Arg | Ser | Leu | Asn | Met | Ala | Tyr | Trp | Gly | |
| | | | | 245 | | | | | 250 | | | | | 255 | | |

| CAA | GGA | ACC | TCA | GTC | ACC | GTC | TCC | TAATAGGATC C | | | | | | | | 803 |
| Gln | Gly | Thr | Ser | Val | Thr | Val | Ser | | | | | | | | | |
| | | | 260 | | | | | | | | | | | | | |

( 2 ) INFORMATION FOR SEQ ID NO:8:

( i ) SEQUENCE CHARACTERISTICS:
  ( A ) LENGTH: 264 amino acids
  ( B ) TYPE: amino acid
  ( D ) TOPOLOGY: linear ( i i ) MOLECULE TYPE: protein ( x i ) SEQUENCE DESCRIPTION: SEQ ID NO:8:

```
Asp Val Glu Ser Pro Leu Ile Ala Lys Val Leu Thr Thr Glu Pro Pro
 1               5                  10                  15
Ile Ile Thr Pro Val Arg Arg Asp Val Val Met Ser Gln Ser Pro Ser
            20                  25                  30
Ser Leu Pro Val Ser Val Gly Glu Lys Val Thr Leu Ser Cys Lys Ser
        35                  40                  45
Ser Gln Ser Leu Leu Tyr Ser Gly Asn Gln Lys Asn Tyr Leu Ala Trp
    50                  55                  60
Tyr Gln Gln Lys Pro Gly Gln Ser Pro Lys Met Met Ile Tyr Trp Ala
 65                 70                  75                  80
Ser Ala Arg Glu Ser Gly Val Pro Asp Arg Phe Thr Gly Ser Gly Ser
            85                  90                  95
Gly Thr Asp Phe Thr Leu Ser Ile Ser Ser Val Lys Thr Glu Asp Leu
        100                 105                 110
Ala Val Tyr Tyr Cys Gln Gln Tyr Tyr Ser Tyr Pro Leu Thr Phe Gly
    115                 120                 125
Ala Gly Thr Lys Leu Val Leu Lys Gly Ser Thr Ser Gly Ser Gly Lys
    130                 135                 140
Ser Ser Glu Gly Lys Gly Gln Val Gln Leu Gln Gln Ser Asp Ala Glu
145                 150                 155                 160
Leu Val Lys Pro Gly Ala Ser Val Lys Ile Ser Cys Lys Ala Ser Gly
            165                 170                 175
Tyr Thr Phe Thr Asp His Ala Ile His Trp Val Lys Gln Asn Pro Glu
        180                 185                 190
Gln Gly Leu Glu Trp Ile Gly Tyr Phe Ser Pro Gly Asn Asp Asp Phe
    195                 200                 205
Lys Tyr Asn Glu Arg Phe Lys Gly Lys Ala Thr Leu Thr Ala Asp Lys
    210                 215                 220
Ser Ser Ser Thr Ala Tyr Val Gln Leu Asn Ser Leu Thr Ser Glu Asp
225                 230                 235                 240
Ser Ala Val Tyr Phe Cys Thr Arg Ser Leu Asn Met Ala Tyr Trp Gly
            245                 250                 255
Gln Gly Thr Ser Val Thr Val Ser
        260
```

( 2 ) INFORMATION FOR SEQ ID NO:9:

( i ) SEQUENCE CHARACTERISTICS:
    ( A ) LENGTH: 900 base pairs
    ( B ) TYPE: nucleic acid
    ( C ) STRANDEDNESS: both
    ( D ) TOPOLOGY: both ( i i ) MOLECULE TYPE: cDNA ( i x ) FEATURE:
    ( A ) NAME/KEY: CDS
    ( B ) LOCATION: 86..784

( x i ) SEQUENCE DESCRIPTION: SEQ ID NO:9:

```
CACACCCTGA CAAGCTGCCA GGCAGGTTCT CTTCCTCTCA CATACTGACC CACGGCTCCA          60
```

| | | | | | | | | | | | | | | | | |
|---|---|---|---|---|---|---|---|---|---|---|---|---|---|---|---|---|
| CCCTCTCTCC | CCTGGAAAGG | ACACC | ATG<br>Met<br>1 | AGC<br>Ser | ACT<br>Thr | GAA<br>Glu | AGC<br>Ser<br>5 | ATG<br>Met | ATC<br>Ile | CGG<br>Arg | GAC<br>Asp | | | | | 112 |
| GTG<br>Val<br>10 | GAG<br>Glu | CTG<br>Leu | GCC<br>Ala | GAG<br>Glu | GAG<br>Glu<br>15 | GCG<br>Ala | CTC<br>Leu | CCC<br>Pro | AAG<br>Lys | AAG<br>Lys<br>20 | ACA<br>Thr | GGG<br>Gly | GGG<br>Gly | CCC<br>Pro | CAG<br>Gln<br>25 | 160 |
| GGC<br>Gly | TCC<br>Ser | AGG<br>Arg | CGG<br>Arg | TGC<br>Cys<br>30 | TTG<br>Leu | TTC<br>Phe | CTC<br>Leu | AGC<br>Ser | CTC<br>Leu<br>35 | TTC<br>Phe | TCC<br>Ser | TTC<br>Phe | CTG<br>Leu | ATC<br>Ile<br>40 | GTG<br>Val | 208 |
| GCA<br>Ala | GGC<br>Gly | GCC<br>Ala | ACC<br>Thr<br>45 | ACG<br>Thr | CTC<br>Leu | TTC<br>Phe | TGC<br>Cys | CTG<br>Leu<br>50 | CTG<br>Leu | CAC<br>His | TTT<br>Phe | GGA<br>Gly | GTG<br>Val<br>55 | ATC<br>Ile | GGC<br>Gly | 256 |
| CCC<br>Pro | CAG<br>Gln | AGG<br>Arg<br>60 | GAA<br>Glu | GAG<br>Glu | TCC<br>Ser | CCC<br>Pro | AGG<br>Arg<br>65 | GAC<br>Asp | CTC<br>Leu | TCT<br>Ser | CTA<br>Leu | ATC<br>Ile<br>70 | AGC<br>Ser | CCT<br>Pro | CTG<br>Leu | 304 |
| GCC<br>Ala | CAG<br>Gln<br>75 | GCA<br>Ala | GTC<br>Val | AGA<br>Arg | TCA<br>Ser | TCT<br>Ser<br>80 | TCT<br>Ser | CGA<br>Arg | ACC<br>Thr | CCG<br>Pro | AGT<br>Ser<br>85 | GAC<br>Asp | AAG<br>Lys | CCT<br>Pro | GTA<br>Val | 352 |
| GCC<br>Ala<br>90 | CAT<br>His | GTT<br>Val | GTA<br>Val | GCA<br>Ala | AAC<br>Asn<br>95 | CCT<br>Pro | CAA<br>Gln | GCT<br>Ala | GAG<br>Glu | GGG<br>Gly<br>100 | CAG<br>Gln | CTC<br>Leu | CAG<br>Gln | TGG<br>Trp | CTG<br>Leu<br>105 | 400 |
| AAC<br>Asn | CGC<br>Arg | CGG<br>Arg | GCC<br>Ala | AAT<br>Asn<br>110 | GCC<br>Ala | CTC<br>Leu | CTG<br>Leu | GCC<br>Ala | AAT<br>Asn<br>115 | GGC<br>Gly | GTG<br>Val | GAG<br>Glu | CTG<br>Leu | AGA<br>Arg<br>120 | GAT<br>Asp | 448 |
| AAC<br>Asn | CAG<br>Gln | CTG<br>Leu | GTG<br>Val<br>125 | GTG<br>Val | CCA<br>Pro | TCA<br>Ser | GAG<br>Glu | GGC<br>Gly<br>130 | CTG<br>Leu | TAC<br>Tyr | CTC<br>Leu | ATC<br>Ile | TAC<br>Tyr<br>135 | TCC<br>Ser | CAG<br>Gln | 496 |
| GTC<br>Val | CTC<br>Leu | TTC<br>Phe<br>140 | AAG<br>Lys | GGC<br>Gly | CAA<br>Gln | GGC<br>Gly | TGC<br>Cys<br>145 | CCC<br>Pro | TCC<br>Ser | ACC<br>Thr | CAT<br>His | GTG<br>Val<br>150 | CTC<br>Leu | CTC<br>Leu | ACC<br>Thr | 544 |
| CAC<br>His | ACC<br>Thr<br>155 | ATC<br>Ile | AGC<br>Ser | CGC<br>Arg | ATC<br>Ile | GCC<br>Ala<br>160 | GTC<br>Val | TCC<br>Ser | TAC<br>Tyr | CAG<br>Gln | ACC<br>Thr<br>165 | AAG<br>Lys | GTC<br>Val | AAC<br>Asn | CTC<br>Leu | 592 |
| CTC<br>Leu<br>170 | TCT<br>Ser | GCC<br>Ala | ATC<br>Ile | AAG<br>Lys | AGC<br>Ser<br>175 | CCC<br>Pro | TGC<br>Cys | CAG<br>Gln | AGG<br>Arg | GAG<br>Glu<br>180 | ACC<br>Thr | CCA<br>Pro | GAG<br>Glu | GGG<br>Gly | GCT<br>Ala<br>185 | 640 |
| GAG<br>Glu | GCC<br>Ala | AAG<br>Lys | CCC<br>Pro | TGG<br>Trp<br>190 | TAT<br>Tyr | GAG<br>Glu | CCC<br>Pro | ATC<br>Ile | TAT<br>Tyr<br>195 | CTG<br>Leu | GGA<br>Gly | GGG<br>Gly | GTC<br>Val | TTC<br>Phe<br>200 | CAG<br>Gln | 688 |
| CTG<br>Leu | GAG<br>Glu | AAG<br>Lys | GGT<br>Gly<br>205 | GAC<br>Asp | CGA<br>Arg | CTC<br>Leu | AGC<br>Ser | GCT<br>Ala<br>210 | GAG<br>Glu | ATC<br>Ile | AAT<br>Asn | CGG<br>Arg | CCC<br>Pro<br>215 | GAC<br>Asp | TAT<br>Tyr | 736 |
| CTC<br>Leu | GAC<br>Asp | TTT<br>Phe<br>220 | GCC<br>Ala | GAG<br>Glu | TCT<br>Ser | GGG<br>Gly | CAG<br>Gln<br>225 | GTC<br>Val | TAC<br>Tyr | TTT<br>Phe | GGG<br>Gly | ATC<br>Ile<br>230 | ATT<br>Ile | GCC<br>Ala | CTG<br>Leu | 784 |
| TGAGGAGGAC | GAACATCAA | CCTTCCCAAA | CGCCTCCCCT | GCCCCAATCC | CTTTATTACC | | | | | | | | | | | 844 |
| CCCTCCTTCA | GACACCCTCA | ACCTCTTCTG | GCTCAAAAAG | AGAATTGGGG | GCTTAG | | | | | | | | | | | 900 |

( 2 ) INFORMATION FOR SEQ ID NO:10:

( i ) SEQUENCE CHARACTERISTICS:
        ( A ) LENGTH: 233 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met<br>1 | Ser | Thr | Glu | Ser<br>5 | Met | Ile | Arg | Asp | Val<br>10 | Glu | Leu | Ala | Glu | Glu<br>15 | Ala |
|---|---|---|---|---|---|---|---|---|---|---|---|---|---|---|---|
| Leu | Pro | Lys | Lys | Thr | Gly | Gly | Pro | Gln | Gly | Ser | Arg | Arg | Cys | Leu | Phe |

```
                        20                          25                              30
Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Ser Pro
    50                  55                  60

Arg Asp Leu Ser Leu Ile Ser Pro Leu Ala Gln Ala Val Arg Ser Ser
65                  70                  75                      80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100             105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( D ) TOPOLOGY: both ( x i ) SEQUENCE DESCRIPTION: SEQ ID NO:11:

```
Gly Ser Gly Lys Pro Gly Ser Gly Glu Gly
1               5                   10
```

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( D ) TOPOLOGY: both ( x i ) SEQUENCE DESCRIPTION: SEQ ID NO:12:

```
Asn Met Ala Tyr Trp Gly Gln Gly Thr Ser Val Thr Val Ser
1               5                   10
```

( 2 ) INFORMATION FOR SEQ ID NO:13:

( i ) SEQUENCE CHARACTERISTICS:
        ( A ) LENGTH: 53 base pairs
        ( B ) TYPE: nucleic acid
        ( C ) STRANDEDNESS: both
        ( D ) TOPOLOGY: both ( x i ) SEQUENCE DESCRIPTION: SEQ ID NO:13:

```
AATATGGCCT ACTGGGGTCA AGGAACCTCA GTCACCGTCT CCTAATAGGA TCC        53
```

(2) INFORMATION FOR SEQ ID NO:14:

(i) SEQUENCE CHARACTERISTICS:
    (A) LENGTH: 11 amino acids
    (B) TYPE: amino acid
    (D) TOPOLOGY: both (xi) SEQUENCE DESCRIPTION: SEQ ID NO:14:

```
Met Val Arg Ser Ser Ser Arg Thr Pro Ser Asp
1               5                   10
```

(2) INFORMATION FOR SEQ ID NO:15:

(i) SEQUENCE CHARACTERISTICS:
    (A) LENGTH: 25 amino acids
    (B) TYPE: amino acid
    (D) TOPOLOGY: both (xi) SEQUENCE DESCRIPTION: SEQ ID NO:15:

```
Asn Met Ala Tyr Trp Gly Gln Gly Thr Ser Val Thr Val Ser Gly Ser
1               5                   10                  15
Arg Ser Ser Ser Arg Thr Pro Ser Asp
            20              25
```

(2) INFORMATION FOR SEQ ID NO:16:

(i) SEQUENCE CHARACTERISTICS:
    (A) LENGTH: 33 amino acids
    (B) TYPE: amino acid
    (D) TOPOLOGY: both (xi) SEQUENCE DESCRIPTION: SEQ ID NO:16:

```
Asn Met Ala Tyr Trp Gly Gln Gly Thr Ser Val Thr Val Ser Gly Ser
1               5                   10                  15
Gly Lys Pro Gly Ser Gly Glu Gly Arg Ser Ser Ser Arg Thr Pro Ser
            20                  25                  30
Asp
```

(2) INFORMATION FOR SEQ ID NO:17:

(i) SEQUENCE CHARACTERISTICS:
    (A) LENGTH: 32 amino acids
    (B) TYPE: amino acid
    (D) TOPOLOGY: both (xi) SEQUENCE DESCRIPTION: SEQ ID NO:17:

```
Asn Met Ala Tyr Trp Gly Gln Gly Thr Ser Val Thr Val Ser Gly Ser
1               5                   10                  15
His His His His His Ser Gly Arg Ser Ser Ser Arg Thr Pro Ser Asp
            20                  25                  30
```

(2) INFORMATION FOR SEQ ID NO:18:

(i) SEQUENCE CHARACTERISTICS:
    (A) LENGTH: 17 amino acids
    (B) TYPE: amino acid
    (D) TOPOLOGY: both (xi) SEQUENCE DESCRIPTION: SEQ ID NO:18:

```
Val Thr Val Ser Gly Ser His His His His Ser Gly Glu Ser Pro
1               5                   10                  15
Leu
```

(2) INFORMATION FOR SEQ ID NO:19:

( i ) SEQUENCE CHARACTERISTICS:
  ( A ) LENGTH: 9 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:19:

Arg Ser Ser Ser Arg Thr Pro Ser Asp
1               5

ANTIGEN-BINDING FUSION PROTEINS

This application is a division of application Ser. No. 08/323,445, filed Oct. 13, 1994, (status pending).

BACKGROUND OF THE INVENTION

1. Field of the Invention

The present invention relates generally to the production of antigen-binding fusion molecules. More specifically, the invention relates to fusion forms of antigen-binding proteins having an immunoeffector moiety and/or a cytolytic moiety, particularly fusion forms having an immunoeffector or cytolytic moiety derived from tumor necrosis factor and/or phospholipase A activating protein. The invention also relates to multivalent fusion forms of antigen-binding proteins. Compositions of, genetic constructions for, methods of use, and methods for producing these antigen-binding fusion proteins are also disclosed.

2. Description of the Background Art

Antibodies are proteins generated by the immune system to provide a specific molecule capable of complexing with an invading molecule, termed an antigen. Natural antibodies have two identical antigen-binding sites, both of which are specific to a particular antigen. The antibody molecule "recognizes" the antigen by complexing its antigen-binding sites with areas of the antigen termed epitopes. The epitopes fit into the conformational architecture of the antigen-binding sites of the antibody, enabling the antibody to bind to the antigen.

The antibody molecule is composed of two identical heavy and two identical light polypeptide chains, held together by interchain disulfide bonds.

Covalent interchain bonding serves to stabilize the various chains of antibody molecules. The prototypical immunoglobulin structure consists of disulfide bonds holding the $C_L$ and $C_H1$ domains together and also holding the hinge regions of the two heavy chains together. The so-called hinge region between the $C_H1$ and $C_H2$ domains contains the cysteine residues that crosslink to form the linkage between the two heavy chains. See, for example, Clark, W. R., *The Experimental Foundations of Modern Immunology*, 2nd Ed., John Wiley & Sons, New York (1983).

The remainder of this discussion on antibodies will refer only to one pair of light/heavy chains, as each light/heavy pair is identical. Each individual light and heavy chain folds into regions of approximately 110 amino acids, assuming a conserved three-dimensional conformation. The light chain comprises one variable region (termed $V_L$) and one constant region ($C_L$), while the heavy chain comprises one variable region ($V_H$) and three constant regions ($C_H1$, $C_H2$ and $C_H3$). Pairs of regions associate to form discrete structures. In particular, the light and heavy chain variable regions, $V_L$ and $V_H$, associate to form an "$F_v$" area which contains the antigen-binding site.

The variable regions of both heavy and light chains show considerable variability in structure and amino acid composition from one antibody molecule to another, whereas the constant regions show little variability. The term "variable" as used in this specification refers to the diverse nature of the amino acid sequences of the antibody heavy and light chain variable regions. Each antibody recognizes and binds antigen through the binding site defined by the association of the heavy and light chain variable regions into an $F_v$ area. The light-chain variable region $V_L$ and the heavy-chain variable region $V_H$ of a particular antibody molecule have specific amino acid sequences that allow the antigen-binding site to assume a conformation that binds to the antigen epitope recognized by that particular antibody.

Within the variable regions are found regions in which the amino acid sequence is extremely variable from one antibody to another. Three of these so-called "hypervariable" regions or "complementarity-determining regions" (CDR's) are found in each of the light and heavy chains. The three CDR's from a light chain and the three CDR's from a corresponding heavy chain form the antigen-binding site.

Cleavage of the naturally-occurring antibody molecule with the proteolytic enzyme papain generates fragments which retain their antigen-binding site. These fragments, commonly known as Fab's (for Fragment, antigen binding site) are composed of the $C_L$, $V_L$, $C_H1$ and $V_H$ regions of the antibody. In the Fab the light chain and the fragment of the heavy chain are covalently linked by a disulfide linkage.

Antibodies have been generated to deliver cells, cytotoxins, or drugs to specific sites. An important use has been to deliver host cytotoxic cells, such as natural killer or cytotoxic T cells, to specific cellular targets. (Staerz et al., *Nature* 314:628 (1985); Songilvilai, et al., *Clin. Exp. Immunol.* 79:315 (1990)). Another important use has been to deliver cytotoxic proteins to specific cellular targets. (Raso et al., *Cancer Res.* 41:2073 (1981); Honda et al., *Cytotechnology* 4:59 (1990)). A further important use has been to deliver anti-cancer non-protein drugs to specific cellular targets (Corvalan et al., *Intl. J. Cancer Suppl.* 2:22 (1988); Pimm et al., *Brit. J. Can.* 61:508 (1990)).

Recent advances in immunobiology, recombinant DNA technology, and computer science have allowed the creation of single polypeptide chain molecules that bind antigen. These single-chain antigen-binding molecules (herein "SCA") incorporate a linker polypeptide to bridge the individual variable regions, $V_L$ and $V_H$, into a single polypeptide chain. A computer-assisted method for linker design is described more particularly in U.S. Pat. No. 4,704,692. A description of the theory and production of single-chain antigen-binding proteins is found in U.S. Pat. Nos. 4,946,778 and 5,260,203. The single-chain antigen-binding proteins produced under the process recited in U.S. Pat. Nos. 4,946,778 and 5,260,203 have binding specificity and affinity substantially similar to that of the corresponding Fab fragment.

Phospholipase A activating protein (herein "PLAP") is a protein that activates phospholipase A, a lipolytic enzyme which hydrolizes the 2-acyl fatty acid ester of glycerophospholipids. This hydrolysis releases arachidonic acid which is converted into a number of biologically active compounds called eicosanoids. PLAP has been postulated to be involved in the inflammatory cascade in certain biological settings, and induces eicosanoid release and stimulation of joint inflammation, related to rheumatoid arthritis. It has also been shown that PLAP stimulates human neutrophil aggregation and the release of lysosomal enzymes, superoxide, and eicosanoids (Bomalaski et al., *J. Immunol.* 142 (11) :3957–3962 (1989).

Further, PLAP activity has been shown to reside in several different gene products and is ubiquitous. The gene encoding PLAP has been cloned from a cDNA library (Clark et al., *Proc. Natl. Acad. Sci. USA* 88:5418–5422 (1991)). Antibodies have also been generated to recombinant PLAP using PLAP-β-galactosidase fusion protein as antigen (Clark et al., *Proc. Natl. Acad. Sci. USA* 88: 5418–5422 (1991)). PLAP shares antigen and functional characteristics with melittin and was originally discovered and isolated through these similarities (Clark et al. *J. Biochem.* 262 (9):4402–4406 (1987)).

Tumor necrosis factors are polypeptide cytokines which serve a critical role as mediators of endotoxin-induced vascular collapse and are involved in certain inflammatory reactions. Two forms of tumor necrosis factor are known—TNF-alpha (or cachectin) and TNF-beta (or lymphotoxin) (Eck et al., *J. Biol. Chem.* 264:17595–17605 (1989)). The human TNF-alpha gene cDNA was cloned and the base sequence was determined (Wang et al., *Science* 228:149–154 (1985)). The pathogenesis of the inflammatory reaction mediated by TNF may involve eicosanoids. Tumor necrosis factor is primarily produced in monocytes and macrophages following activation by endotoxin as well as other inflammatory and immune stimuli. TNF is known to be an agent responsible for hemorrhagic necrosis of experimental tumors. It is also a likely candidate responsible for the mediation of cachexia, septic shock, and certain other inflammatory reactions. TNF has been shown to induce the manifold effects of bone resorption, eicosanoid synthesis, collagenase production, vasculitis, and hemorrhagic necrosis of transplanted tissues (Van den Boch, H., *Biochem. Biophys. Acta.* 604:191–246 (1980)).

The vascular endothelial lining is important in regulating the permeability and structure of blood vessels. Further, morphological and biological activities of the vasculature can be modified in response to changes in endothelial cell structure (Bell et al., *Proc. Natl. Acad. Sci. USA* 76:32–38–3241 (1979); Chau et al., *Biochem. Biophys. Res. Commun.* 100:1688–1695 (1981); Clark et al., *J. Biol. Chem.* 261:10713–10718 (1986); Clark et al., *Biochem. J.* 250:125–132 (1988)). TNF may interact with the endothelial cell lining to cause some of its many effects. TNF has been reported to increase the synthesis of eicosanoids (Aderem et al., *J. Exp. Med.* 163:139–154 (1986); Burch et al., *Proc. Natl. Acad. Sci. USA* 83:7201–7205 (1986); Burch et al., *Proc. Natl. Acad. Sci. USA* 84:6374–6378 (1987); Clark et al., *Eur. J. Pharmacol.* 116:207–220 (1985); Clark et al., *Prostaglandins* 31:157–166 (1986)). Certain eicosanoids are known to effect the vasculature. It is therefore likely that TNF mediates certain of its biological effects through increased eicosanoid synthesis following stimulation of endothelial cells. Elaboration of eicosanoids in response to TNF stimulation may affect cells in close proximity to those releasing the eicosanoids or may act on more distant cellular targets. TNF was shown to induce phospholipase $A_2$ activity and synthesis of a phospholipase $A_2$-activating protein in endothelial cells (Clark et al., *Biochem. J.* 250:125–132 (1988)).

There is some evidence that TNF is effective in the treatment of parasitic disease (Wozencroft et al., *Infect. Immun.* 43:664 (1984)).

Fusion proteins have traditionally been utilized to merge characteristics inherent in different proteins into the same molecule. This methodology allows for the production of useful multifunctional molecules. These molecules have been used for many purposes.

Fusion proteins consisting of a single-chain antibody fused to interleukin-2 have been reported (Savage, P., *The Third Annual IBC International Conference on Antibody Engineering: New Technology and Application Implications*, International Business Communications, Southborough, Mass. (1992)).

It has also been reported that fusion antibodies have been constructed using interleukin-2, GM-CSF and TNFs α and β fused to the carboxyl terminus (herein "C terminus") of a chimeric anti-ganglioside antibody (ch14.18) and expressed in transfected hybridoma cells (Gillies et al., *Bioconj. Chem.* 4(3):230–235 (1993)). Moreover, this chimeric anti-ganglioside antibody fused to interleukin-2 was shown to stimulate T-cell killing of tumor cells (Gillies et al., *Bioconj. Chem.* 4(3):230–235 (1993)).

It has also been reported that enhanced tumor uptake of two different monoclonal antibodies can be induced by an IL-2 immunoconjugate (LeBarthon et al., *Can. Res.* 51: 2694–2698 (1991)).

Single chain polypeptide molecules capable of binding antigen which include a separate functional polypeptide sequence have been described (U.S. Pat. No. 5,132,405). Multimers containing these multifunctional proteins have also been described (PCT WO 88/09344).

Advances in protein design and construction have recently allowed for the production of rationally-designed, intramolecular-bond stabilized proteins. A computer-assisted method for identifying amino acid residues amenable to replacement by cysteine residues to promote the formation of a protein-stabilizing disulfide bond is found in U.S. Pat. No. 4,908,773.

SUMMARY OF THE INVENTION

This invention relates to the discovery that single-chain antigen-binding fusion proteins having an immunoeffector or cytolytic moiety have significant utility beyond that of single-chain antigen-binding proteins. Immunoeffector and cytolytic antigen-binding fusion proteins have more than an antigen-binding site activity or function. An immunoeffector or cytolytic moiety on the fusion antigen-binding protein will impart upon the protein certain or all of the immunoeffector or cytolytic attributes of the fusion partner or partners. Other novel uses of immunoeffector and cytolytic antigen-binding fusion proteins have been demonstrated or are envisioned here.

Accordingly, the invention is directed to single-chain and multivalent immunoeffector and cytolytic antigen-binding fusion proteins, compositions of single-chain and multivalent immunoeffector and cytolytic antigen-binding fusion proteins, methods of making and purifying single-chain and multivalent immunoeffector and cytolytic antigen-binding fusion proteins, and uses for single-chain and multivalent immunoeffector and cytolytic antigen-binding fusion proteins. The invention provides an immunoeffector or cytolytic antigen-binding fusion protein having at least one single-chain antigen-binding protein molecule. Each single-chain antigen-binding molecule has a first polypeptide and a second polypeptide joined by a linker. Each of the polypeptides has the binding portion of the variable region of an antibody heavy or light chain. An immunoeffector polypeptide or a cytolytic polypeptide is fused to at least one of the first or second polypeptides or the peptide linker. It is preferred that the immunoeffector polypeptide or a cytolytic polypeptide is selected from the group consisting of: TNF, an immunoeffector or cytolytic fragment of TNF, PLAP, and an immunoeffector or cytolytic fragment of PLAP.

Also provided is an antigen-binding fusion protein as described above further having an immunoeffector or cytolytic fragment of IL-2 fused to at least one of the first or second polypeptides or the peptide linker.

Further provided is a genetic sequence which codes for the single-chain fusion protein having a first DNA sequence coding for the $V_L$ or $V_H$ of a CC49 monoclonal antibody polypeptide, a second DNA sequence coding for the $V_L$ or $V_H$ of a CC49 monoclonal antibody polypeptide, a DNA sequence coding for a peptide linker linking the first and second polypeptides into the single-chain protein, and a DNA sequence coding for an immunoeffector polypeptide or cytolytic polypeptide fused to a DNA sequence coding for any one of the first or second polypeptides, or the linker peptide.

It is preferred in any of the embodiments of the invention that the first polypeptide has the binding portion of the variable region of an antibody light chain, and the second polypeptide has the binding portion of the variable region of an antibody heavy chain.

It is also preferred in any of the embodiments of the invention that the first polypeptide has the binding portion of the variable region of an antibody light chain, and the second polypeptide has the binding portion of the variable region of an antibody light chain.

It is further preferred in any of the embodiments of the invention that the first polypeptide has the binding portion of the variable region of an antibody heavy chain, and the second polypeptide has the binding portion of the variable region of an antibody heavy chain.

Another embodiment of the invention is a composition having an antigen-binding fusion protein, particularly a protein having two immunoeffector domains, two polypeptides capable of mediating cytolysis, or a combination of two of these polypeptides.

It is preferred that the compositions of the invention contain a pharmaceutically acceptable carrier or diluent.

It is more preferred in the compositions having multivalent fusion proteins that the first polypeptide has the binding portion of the variable region of an antibody light chain, and the second polypeptide has the binding portion of the variable region of an antibody heavy chain.

It is also more preferred in the compositions having multivalent fusion proteins that the first polypeptide has the binding portion of the variable region of an antibody light chain, and the second polypeptide has the binding portion of the variable region of an antibody light chain.

It is further more preferred in the compositions having multivalent fusion proteins that the first polypeptide has the binding portion of the variable region of an antibody heavy chain, and the second polypeptide has the binding portion of the variable region of an antibody heavy chain.

Another aspect of the invention includes a method of killing tumor cells in or suspected of being in an individual, which has the steps of contacting the individual with an immunoeffector or cytolytic antigen-binding fusion protein.

Also provided is a multivalent antigen-binding fusion protein having at least two single-chain immunoeffector or cytolytic antigen-binding fusion proteins. In these molecules, each of the fusion proteins has a first polypeptide with a binding portion of the variable region of an antibody heavy or light chain, a second polypeptide with the binding portion of the variable region of an antibody heavy or light chain, and a peptide linker linking the first and second polypeptides into the single-chain molecule. At least one of the single-chain molecules in this multivalent molecule further has an immunoeffector polypeptide or cytolytic polypeptide fused to at least one peptide of the first or second polypeptides or the peptide linker. It is preferred that the immunoeffector or cytolytic polypeptide is selected from the group consisting of: TNF, an immunoeffector or cytolytic fragment of TNF, PLAP, and an immunoeffector or cytolytic fragment of PLAP.

Also provided is a single-chain fusion protein having a first and second polypeptide each of which has the binding portion of the variable region of an antibody light chain, and a peptide linker linking the first and second polypeptides as described above. An immunoeffector polypeptide or cytolytic polypeptide is fused to at least one peptide of the first or second polypeptides or peptide linker. The immunoeffector polypeptide or cytolytic polypeptide is selected from the group consisting of TNF, an immunoeffector or cytolytic fragment of TNF, PLAP, and an immunoeffector or cytolytic fragment of PLAP. A similar molecule is provided differing only by having two binding portions of the variable region of an antibody heavy chain instead of binding portions from the light chain.

A preferred embodiment of the invention is a DNA coding for a single-chain fusion protein having a $V_L$ and $V_H$ of a CC49 monoclonal antibody joined by a peptide linker as described above. A DNA sequence coding for an immunoeffector polypeptide or cytolytic polypeptide is fused to at least one DNA sequence coding for the $V_L$ or $V_H$ peptide or the peptide linker. The imnmunoeffector polypeptide or cytolytic polypeptide is selected from the group consisting of TNF, an immunoeffector or cytolytic fragment of TNF, PLAP, and an immunoeffector or cytolytic fragment of PLAP.

Further provided is an antigen-binding fusion proteins wherein the immunoeffector polypeptide or cytolytic polypeptide has the sequence Glu Ser Pro Leu Ile Ala Lys Val Leu Thr Thr Glu Pro Pro Ile Ile Thr Pro Val Arg Arg (SEQ ID NO:1).

Also provided is an antigen-binding fusion protein wherein the peptide spacer has a sequence selected from the group consisting of: Gly Ser; and Gly Ser Gly Lys Pro Gly Ser Gly Glu Gly (SEQ ID NO:11).

A further embodiment of the invention is an antigen-binding fusion protein wherein the peptide spacer has the sequence Gly Ser His His His His His Ser Gly (SEQ ID NO:2).

Also provided is a multivalent antigen-binding fusion protein wherein at least one of the peptide spacers has a sequence selected from the group consisting of: Gly Ser, Gly Ser His His His His His Ser Gly (SEQ ID NO:2) and Gly Ser Gly Lys Pro Gly Ser Gly Glu Gly (SEQ ID NO:11).

Also provided is a genetic sequence which codes for a single-chain fusion protein. The DNA sequence has a sequence coding for a first polypeptide having the binding portion of the variable region of an antibody light or heavy chain. The DNA sequence also has a sequence coding for a second polypeptide having the binding portion of the variable region of an antibody light or heavy chain. The DNA sequence also has a sequence which codes for a peptide linker linking the first and second polypeptides into the single-chain protein. The fusion portion of the DNA sequence codes for and an immunoeffector polypeptide fused to at least a DNA sequence which codes for one peptide of the first or second polypeptides or peptide linker. It is preferred that the immunoeffector or cytolytic polypeptide is selected from the group consisting of: TNF, an immunoeffector or cytolytic fragment of TNF, PLAP, and an immunoeffector or cytolytic fragment of PLAP.

A preferred genetic sequence of the invention codes for another single-chain fusion protein. This embodiment has a first DNA sequence coding for the $V_L$ or $V_H$ of a CC49 monoclonal antibody linked to a second DNA sequence coding for the $V_L$ or $V_H$ of a CC49 monoclonal antibody and a DNA sequence coding for a peptide linker linking the first and second $V_L$ or $V_H$ into a single-chain protein. The linked DNA molecule also has a DNA sequence coding for an immunoeffector polypeptide fused to at least one DNA coding for the first or second polypeptides or peptide linker. It is preferred that the immunoeffector is selected from the group consisting of: TNF, an immunoeffector or cytolytic fragment of TNF, PLAP, and an immunoeffector or cytolytic fragment of PLAP.

Another aspect of the present invention includes the genetic constructions encoding the combinations of regions $V_L$-$V_L$ and $V_H$-$V_H$ for single-chain fusion molecules, and other constructs encoding multivalent immunoeffector antigen-binding fusion proteins.

Also included are replicable cloning or expression vehicles including plasmids, hosts transformed with the aforementioned genetic sequences, and methods of producing proteins with the sequences, transformed hosts, and expression vehicles.

Methods of use are provided, such as a method of using the protein as a carrier to treat pathologies of specific bodily organs of an animal, a therapeutic method of using the protein to treat a medical condition, and an immunotherapeutic method of conjugating a protein with a therapeutically or diagnostically effective agent.

An advantage of using antigen-binding fusion proteins of the present invention instead of fused or conjugated whole antibodies, is the enhanced clearing of the antigen-binding fusion proteins from the blood due to their smaller size as compared to fused or conjugated whole antibodies which may afford lower background in imaging applications. Antigen-binding fusion proteins may penetrate solid tumors better than fusion proteins containing whole antibodies, resulting in better tumor-fighting ability. Also, because they are smaller and lack the constant domains of intact antibodies, the antigen-binding fusion proteins of the present invention may be less immunogenic than fusion proteins containing whole antibodies. The constant domains of whole antibodies also contain binding sites for liver, spleen and certain other cells and their absence should thus reduce accumulation in non-target tissues.

Another advantage of antigen-binding fusion proteins of the present invention is the ease with which they may be produced and engineered, as compared to the myeloma-fusing technique pioneered by Kohler and Milstein that is used to produce whole antibodies combined with the cumbersome techniques of conjugating proteins to whole antibodies.

BRIEF DESCRIPTION OF THE DRAWINGS

The present invention as defined in the claims can be better understood with reference to the text and to the following drawings:

FIG. 1A depicts monovalent antigen binding fusion molecules, bound to antigens, having either an immunoeffector or cytolytic moiety (illustrated as a helix) fused to the $V_L$ domain. Also depicted is a monovalent antigen binding fusion molecule having either an immunoeffector or cytolytic moiety (illustrated as a helix with a sawtooth terminus) fused to the $V_H$ domain.

FIG. 1B illustrates a bivalent antigen-binding fusion protein wherein each monomeric subunit is a fusion protein. The two fusion partners are different in this fusion protein.

FIG. 1C depicts a bivalent antigen-binding fusion molecule wherein only a one of a monomeric subunit is a fusion protein. This fusion protein monomer comprises two different immunoeffector or cytolytic moieties, one on the $V_L$ domain and one on the $V_H$ domain.

FIG. 2A illustrates a dimeric molecule, each subunit having a different immunoeffector or cytolytic moiety fused in the linker.

FIG. 2B depicts a trimeric molecule. One of the monomeric subunits is not a fusion molecule, and the other two monomeric subunits are fusion proteins.

FIG. 3A depicts a homobivalent antigen-binding fusion protein wherein each of the $V_L$ domains is fused to an immunoeffector or cytolytic moiety. The fusion protein is shown bound to antigen.

FIG. 3B depicts a heterobivalent molecule wherein two different immunoeffector or cytolytic moieties are present. One is fused to a $V_L$ domain and the other is fused to a $V_H$ domain.

FIG. 3C depicts a trivalent antigen-binding fusion protein wherein an immunoeffector or cytolytic moiety is fused to one of the variable domains of each single-chain fusion protein. The multivalent molecule is associated by interactions within the protein sequence of the immunoeffector domain. It is contemplated that a trimeric antigen-binding fusion protein comprising TNF, which naturally forms trimers, may associate in this way.

FIGS. 4A–B illustrates the DNA (SEQ ID NO:3) and amino acid (SEQ ID NO:4) sequence of CC49/212 SCA with a PLAP C-terminus.

FIGS. 5A–B illustrates the DNA (SEQ ID NO:5) and amino acid (SEQ ID NO:6) sequence of CC49 $V_L$-PLAP-CC49 $V_H$ SCA.

FIGS. 6A–B depicts the DNA (SEQ ID NO:7) and amino acid (SEQ ID NO:8) sequence of CC49/212 SCA with PLAP N-terminus.

FIGS. 8A–B depicts the cDNA (SEQ ID NO:9) and amino acid (SEQ ID NO:10) sequence of human TNF-alpha. The arrow indicates the border between the amino terminal amino acid (valine, boxed) of mature TNF and the most preferred sequence (beginning with arg) used in the constructs. The most preferred sequence is from this amino terminal arg to the carboxyl terminal amino acid.

FIGS. 9A–E depicts examples of certain SCA-TNF and SCA-PLAP constructs (SEQ ID NOS: 12–18). Only certain fusion portions of the TNF, PLAP and SCA domains are depicted in the examples in 9A–9E. The $V_L$ domain is positioned in the example constructs as shown in the schematic in 9D.

FIG. 9A depicts an SCA-TNF construct (SEQ ID NOS:12–15) where the two amino terminal amino acid residues are removed from a genetically modified form of TNF and the truncated TNF is fused to CC49 sFv.

FIG. 9B depicts an SCA-TNF construct (SEQ ID NO:16) having the truncated TNF of FIG. 9A and a 10mer spacer.

FIG. 9C depicts an SCA-TNF construct (SEQ ID NO:17) having the truncated TNF of FIG. 9A and a spacer containing (His)$_5$ for metal ion purification of the protein.

FIG. 9D depicts a schematic of an SCA-PLAP construct where PLAP is connected to the SCA using a spacer. Similar constructs are provided by the invention using TNF instead of PLAP.

FIG. 9E depicts a schematic of an SCA-PLAP construct (SEQ ID NO:18) where PLAP is connected to the SCA via a spacer containing (His)$_5$ for metal ion purification of the protein.

DETAILED DESCRIPTION OF THE PREFERRED EMBODIMENTS

I. Fusion Constructs

Figure 1A:
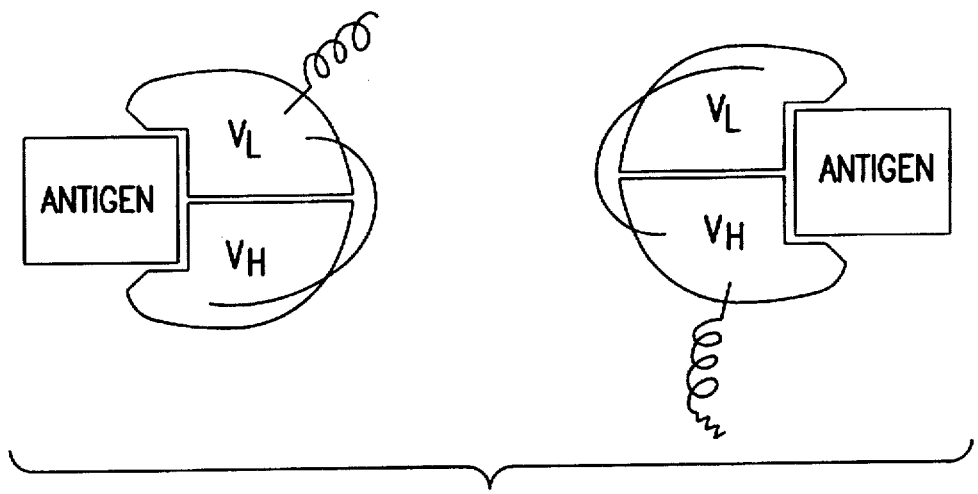
FIGS. 1A–C illustrate a schematic of monovalent and multivalent antigen-binding proteins of the invention.

This invention relates to the discovery that single-chain and multivalent antigen-binding fusion proteins have significant utility beyond that of single-chain antigen-binding proteins. An antigen-binding fusion protein provides the binding capability of the antigen-binding protein combined with the immunoeffector or cytolytic function of the immunoeffector fusion partner or the cytolytic fusion partner.

The terms "antigen-binding fusion," "single-chain fusion," "single-chain antigen-binding fusion," "single-chain immunoeffector fusion," and "single-chain cytolytic fusion" describe fusion proteins that are structurally defined as having the binding portion of a first polypeptide from a variable region of an antibody, associated with the binding portion of a second polypeptide from a variable region of an antibody, the two polypeptides being joined by a peptide linker into a single polypeptide chain, and an immunoeffector or cytolytic polypeptide. The binding portions may associate to form a functional antigen-binding site, as in the case wherein the binding portions are from a light-chain and a heavy-chain variable region pair with appropriately paired complementarity determining regions (CDRs). In this case, the single-chain protein is referred to as a "single-chain antigen-binding immunoeffector fusion" or "single-chain antigen-binding cytolytic fusion." It is preferred that the immunoeffector or cytolytic polypeptide is selected from the group consisting of TNF, an immunoeffector or cytolytic fragment of TNF, PLAP, and an immunoeffector or cytolytic fragment of PLAP, and fused to the single-chain protein. It is most preferred in the TNF fusion constructs that a human TNF gene is used to derive the immunoeffector region of the construct (see Wang et al., *Science* 228:149–154 (1985) for an example of a sequence of a human TNF cDNA).

Alternatively, the binding portions in the fusion molecule may have unnaturally paired CDRs or may both be derived from the same kind of antibody chain, either heavy or light, in which case the resulting single-chain molecule may not display a functional antigen-binding fusion site. Two such fusion molecules may be combined to give a multivalent fusion molecule.

As used herein the term "immunoeffector" refers generally to a peptide, peptide fragment or peptidyl moiety capable of causing or modulating an immune response in an organism. The immunoeffector peptide, peptide fragment or peptidyl moiety useful in the fusion proteins of the invention include, for example, TNF, an immunoeffector fragment of TNF, IL-2, an immunoeffector fragment of IL-2, GM-CSF, an immunoeffector fragment of GM-CSF, PLAP, and an immunoeffector fragment of PLAP. The immune response caused or modulated by the immunoeffector peptide, peptide fragment or peptidyl moiety of the invention includes, for example, the infiltration of immune cells to the site of the peptide, peptide fragment or peptidyl moiety, such as, for example infiltration by T cells, B cells, macrophages and other lymphocytes. The immunoeffector compounds or moieties in the fusion molecules of the invention can also cause or modulate, for example, the activation of lymphocyte cells, the expression of lymphocyte-specific compounds, the elaboration of antibodies, the enhancement of phagocytosis by phagocytes, and the enhancement of tumor cell lysis.

As used herein the term "cytolytic," as used to refer to a peptide, refers generally to a peptide, peptide fragment or peptidyl moiety capable of causing or modulating cytolysis or cell killing. The cytolytic peptide, peptide fragment or peptidyl moiety useful in the fusion proteins of the invention include, for example, TNF, a cytolytic fragment of TNF, IL-2, a cytolytic fragment of IL-2, GM-CSF, a cytolytic fragment of GM-CSF, PLAP, and a cytolytic fragment of PLAP. The cytolysis process caused or modulated by the cytolytic peptide, peptide fragment or peptidyl moiety of the invention encompasses a host of biological effects, including, for example, the infiltration of cytolytic cells and factors to the site of the peptide, peptide fragment or peptidyl moiety, such as, for example T cells, NK cells, tumor infiltrating lymphocytes, macrophages and other lymphocytes. The cytolytic compounds or moieties in the fusion molecules of the invention can also cause or modulate, for example, direct killing of target cells, the activation of lymphocyte and killer cells, the expression of lymphocyte-specific compounds, the enhancement of phagocytosis by phagocytes, and the enhancement of tumor cell lysis.

It is preferred that the single-chain antigen binding proteins of the invention be constructed in one of three forms. The first form comprises a single-chain antigen binding molecule fused at its C terminus to a spacer which is fused to an immunoeffector or cytolytic protein moiety at the C terminus of the spacer, so that the structure will generally be: NH$_2$-V$_L$-linker-V$_H$-spacer-immunoeffector moiety-COOH or NH$_2$-V$_L$-linker-V$_H$-spacer-cytolytic moiety-COOH. The second form comprises the immunoeffector or cytolytic moiety fused to the N-terminus of the single-chain antigen binding protein, having the general structures. NH$_2$-immunoeffector moiety-spacer-V$_L$-linker-V$_H$-COOH or NH$_2$-cytolytic moiety-spacer-V$_L$-linker-V$_H$-COOH. The third general form will have an immunoeffector or cytolytic moiety within the linker joining the variable and variable light chains of the single-chain binding protein, following the general structure: NH$_2$-V$_L$-linker-immunoeffector moiety-linker-V$_1$H, NH$_2$-V$_L$-linker-immunoeffector moiety-V$_H$-COOH, NH$_2$-V$_L$-immunoeffector moiety-linker-V$_H$-COOH, NH$_2$-V$_L$-immunoeffector moiety-V$_H$-COOH, NH$_2$-V$_L$-linder-cytolytic moiety-linker-V$_H$, NH$_2$-V$_L$-linker-cytolytic moiety-V$_H$-COOH, NH$_2$-V$_L$-cytolytic moiety-linker-V$_H$-COOH, or NH$_2$-V$_L$-cytolytic moiety-V$_H$-COOH.

II. Fusion Construct Linkers and Spacers

Linkers used in the fusion constructs of the invention can be any of those linkers known or used in the art. Skilled artisans will be able to determine the appropriate linker to be used for a particular construct. It is preferred that the linkage utilized in constructing antigen-binding fusion proteins of the invention that the linkers be selected from those disclosed in U.S. patent application Ser. No. 07/989,846.

It is preferred that the linkers utilized in constructing the antigen-binding fusion proteins of the invention are between 0 and 50 amino acids in length.

It also is preferred that the linkers are between 0 and 18 amino acids in length in the single-chain proteins within the multivalent forms, and between 18 and 50 amino acids in length for the single-chain molecules that will remain monomeric forms.

In some cases it may be necessary to separate the antigen-binding part of a fusion protein from the immunoeffector of cytolytic part of the fusion protein by a peptide spacer, in order to preserve both activities of the fusion protein. It is preferred that the spacers are between 0 and 50 amino acids in length.

It is further preferred that a spacer having a (histidine)₅ (herein "(His)₅") stretch be used in the single-chain fusion molecules of the invention. These (His)₅ spacer containing molecules will be easily purified by affinity purification using a column having bound metal ions, such as, for example zinc or nickel. This spacer can also be used in multivalent fusion molecules of the invention and can be used to purify multivalent constructs.

It is most preferred that the (His)₅ spacer have the sequence Gly Ser His His His His His Ser Gly (SEQ ID NO:2).

It is also more preferred that the (His)₅ spacer (shown in bold below) be inserted between a serine residue of CC49 $V_H$ and a glutamate residue of the PLAP moiety, so that the structure will be as follows: ... (CC49) ... Val Thr Val Ser Gly Ser His His His His His Ser Gly Glu Ser Pro Leu ... (PLAP) ... (SEQ ID NO:2).

It is also preferred in the fusion molecules of the invention that the spacers be between 2 and 10 amino acid residues in length. A preferred 2-mer spacer is Gly Ser and a preferred 10-mer spacer is Gly Ser Gly Lys Pro Gly Ser Gly Glu Gly (SEQ ID NO:11).

III. PLAP Antigen-binding Fusion Constructs

One of the principal problems in cancer therapy is the reduction of necrotic areas in cell tumors. Necrotic areas arise in tumors from the inability of macrophages to remove these dying cells. The inventors have discovered compounds and methods that will facilitate debulking by targeting activated macrophages to necrotic tissues. Tumor necrosis therapy using radiolabeled anti-histone monoclonal antibodies has been used to target dying cells (U.S. Pat. Nos. 5,019,368 and 4,861,581). The PLAP fusion molecules of the invention will have the advantages of single-chain antigen binding molecules described above.

The inventors have further discovered that PLAP is a potent activator of macrophages and will be useful as a tumor debulking agent when fused to single-chain antigen binding proteins. The ability of single-chain proteins to penetrate into tumors will enhance the effectiveness of a macrophage activating protein, such as, for example, PLAP.

Moreover, the PLAP single-chain antibody fusion proteins will be able to bind certain tumors and activate a localized immune response to the tumors.

The immunoeffector or cytolytic fragment of PLAP useful in the methods of the invention can be determined by measuring PLAP activity. The PLAP activity of the fusion proteins of the invention can be determined using any assay known in the art for measuring PLAP activity. It is preferred that the PLAP activity of the fusion proteins produced be measured using the previously described assay (Clark et al., *Biochem. J.* 250:125–132 (1988); Clark et al., *J. Biol. Chem.* 262:4402–4406 (1987); Clark et al., *Proc. Natl. Acad. Sci. USA* 88:5418–5422 (1991)). For example, the fusion proteins can be examined for their ability to stimulate phospholipase $A_2$ activity in $BC3H_1$ cell sonicates. Activation of phospholipase $A_2$ can be plotted as the fold stimulation of the enzyme activity versus fusion protein concentration. From these data, the dose dependence of phospholipase $A_2$, activity as a function of fusion protein concentration can be calculated. See, for example, Clark et al., *J. Biochem.* 261:10713–10718 (1986); Bomalaski et al., *J. Immunol.* 142: 3957–3962 (1989); Bomalaski et al., *J. Lab. Clin. Med.* 166:184–925 (1990)).

It is preferred that the PLAP fragment in the fusion proteins of the invention have a twenty-one amino acid peptide having the sequence Glu Ser Pro Leu Ile Ala Lys Val Leu Thr Thr Glu Pro Pro Ile Ile Thr Pro Val Arg Arg (SEQ ID NO:1).

Moreover, three basic designs are preferred for PLAP fusion proteins. One general design has a PLAP moiety at the C-terminus of a single-chain antigen binding molecule, one has a PLAP moiety at the N-terminus of the single-chain antigen binding molecule, and one has a PLAP moiety within the linker. It is most preferred that the first and second polypeptides of the single-chain antigen-binding molecule are derived from the CC49 monoclonal antibody (See Muraro et al., *Can. Res.* 48:4588–4596 (1988) for a description of the antibody).

As with all fusion molecules of the invention any of these PLAP fusion molecules can be used as monomeric subunits of multivalent molecules.

IV. TNF Antigen-Binding Fusion Constructs

At one time, the use of TNF showed promise as an anti-cancer therapeutic agent, but in clinical trials TNF has been shown to have severe toxicity. By targeting the TNF to tumor cells using a single-chain antigen binding molecule fused to an active moiety of TNF, lower doses of the TNF activity could be used, thereby avoiding or reducing toxicity.

Figures 9C, 9D, 9E:
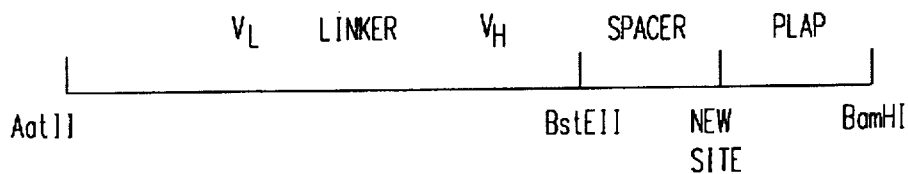

It is preferred that fusion molecules having an immunoeffector or cytolytic moiety at the C-terminus of the antigen-binding molecule be constructed in one of three general ways. The first structure has a ten amino acid residue spacer between the antigen-binding molecule and TNF (see FIG. 9B for example). The second general construct has a spacer containing a five histidine stretch (see FIG. 9C for example). The third general structure has a two amino acid residue spacer (see FIG. 9A for example). Other structures than depicted in FIG. 9 are provided by the invention. It is most preferred that the immunoeffector or cytolytic moiety in these three general structures be derived from TNF.

The crystal structure of TNF reveals that the side chain of the C-terminal Leu 157 is involved in the packing of the TNF trimer. The N-terminus of TNF is conformationally less restricted. Moreover, the first five amino acid residues of all three TNF molecules in the TNF trimer are disordered in the crystal structure. It has been shown that residues can be removed from the N-terminal of TNF and the resulting molecule will still maintain TNF activity. However, removal of residues from the C-terminus of TNF without a concomitant loss of activity has not been shown. Therefore, fusion molecules having the immunoeffector region of TNF are preferably derived from the C-terminal domain of TNF or from molecules having N-terminal deletions.

Expression of TNF in *E. coli* requires the deletion of the leader sequence (Wang et al., *Science* 228:149–154 (1985)). Thus it is preferred that the TNF fusion molecules of the invention have no signal sequence. Skilled artisans will be able to exploit the techniques for constructing active TNF fragments taught by Wang et al., *Science* 228:149–154 (1985) to make certain of the TNF fusion molecules of the invention. Skilled artisans will also be able to use this teaching as a starting point for the creation of other TNF fusion constructs within the scope of the invention.

In view of the observations regarding TNF structure and activity, it is preferred that the TNF fragment used as the fusion partner in the constructs of the invention lack the ultimate N-terminal residue (Val 77 in FIGS. 8A–B). The invention also provides a construct having the TNF sequence beginning with $NH_2$-Arg Ser Ser Ser Arg Thr Pro Ser Asp ... (SEQ ID NO:15) fused to the carboxyl terminus of the single-chain antigen-binding protein (see FIGS. 9A–C (SEQ ID NOS:12–17), for example).

Another preferred construct has the immunoeffector or cytolytic region of TNF, or the TNF sequence beginning with NH$_2$-Arg Ser Ser Ser Arg Thr Pro Ser Asp ... (SEQ ID NO:19) fused to the carboxyl terminus of a CC49 sFv construct, particularly a construct with a 2-mer or 10-mer spacer (see FIGS. 9A–B (SEQ ID NOS:12–16), for example).

Another preferred construction comprises a His$_5$ sequence in the spacer useful for metal ion affinity purification. The construct comprises a TNF sequence beginning with NH$_2$-Arg Ser Ser Ser Arg Thr Pro Ser Asp ... (SEQ ID NO:19) fused to the carboxyl terminus of the spacer, which is fused to the carboxy terminus of the single-chain antigen-binding protein (see FIG. 9C (SEQ ID NO:17), for example).

As with all fusion molecules of the invention any of these TNF fusion molecules can be used as monomeric subunits of multivalent molecules.

V. Multivalent Constructs

For the purposes of this application, "valent" refers to the numerosity of antigen binding sites. Thus, a bivalent protein refers to a protein with two binding sites. Enhanced binding and immunoeffector activity, bi- and multi-specific binding, and other novel uses of antigen-binding fusion proteins have been demonstrated or are envisioned here. Accordingly, the invention is directed to univalent and multivalent forms of antigen-binding fusion proteins, compositions of multivalent and univalent antigen-binding fusion proteins, methods of making and purifying multivalent and univalent forms of antigen-binding fusion proteins, and new and improved uses for multivalent forms of antigen-binding fusion proteins. The invention provides an antigen-binding fusion protein having at least one single-chain immunoeffector protein molecule, each single-chain immunoeffector molecule having a first polypeptide having the binding portion of the variable region of an antibody heavy or light chain; a second polypeptide having the binding portion of the variable region of an antibody heavy or light chain; a peptide linker linking the first and second polypeptides into a single-chain protein and an immunoeffector polypeptide selected from the group consisting of TNF, an immunoeffector or cytolytic fragment of TNF, PLAP, and an immunoeffector or cytolytic fragment of PLAP, and fused to the antigen-binding protein.

VI. Constructs Having More Than One Immunoeffector Moiety

A. Single-Chain Constructs

Provided by the present invention are single-chain antigen-binding fusion proteins further having more than one immunoeffector polypeptide. It is preferred that these single-chain antigen-binding fusion proteins have two immunoeffector polypeptides, particularly combinations including two immunoeffector regions of PLAP, two immunoeffector regions of TNF, and one immunoeffector region of TNF and one immunoeffector region of PLAP fused onto the same single-chain antigen-binding fusion protein.

B. Multivalent Constructs

The invention provides any assemblage, covalently or non-covalently joined, of two or more single-chain immunoeffector proteins, the assemblage having more than one antigen-binding site. The single-chain proteins composing the assemblage may have antigen-binding activity, or they may lack antigen-binding activity individually but be capable of assembly into active immunoeffector antigen-binding fusion proteins. Moreover, multivalent molecules may have single-chain proteins all of which are fused to an immunoeffector polypeptide or certain of which are not fused to an immunoeffector polypeptide. Different immunoeffector polypeptides may be present on individual single-chain proteins constituting a multivalent molecule. For example, a multivalent molecule may be comprised of a first single-chain protein fused to an immunoeffector portion of TNF, a second single-chain protein fused to an immunoeffector portion of PLAP, and a third non-fusion single-chain protein. The term "multivalent" encompasses bivalent, trivalent, tetravalent, etc. It is envisioned that forms above bivalent may be useful for certain applications. The multivalent antigen-binding protein molecule is more fully described in U.S. patent application Ser. No. 07/989,846.

A preferred form of the immunoeffector antigen-binding fusion protein comprises bivalent proteins, including heterobivalent and homobivalent forms. The term "bivalent" means an assemblage of single-chain proteins associated with each other to form two antigen-binding sites. The term "heterobivalent" indicates antigen-binding fusion proteins that are bispecific molecules capable of binding to two different antigenic determinants. Therefore, heterobivalent proteins have two antigen-binding sites that have different binding specificities. The term "homobivalent" indicates that the two binding sites are for the same antigenic determinant.

Homobivalent and heterobivalent forms may be comprised of a single-chain protein, each of which is fused to an immunoeffector polypeptide, as well as molecules having two single-chain proteins only one of which is fused to an immunoeffector polypeptide. For example, heterobivalent and homobivalent molecules may have a first single-chain protein fused to an immunoeffector portion of TNF and a second single-chain protein fused to an immunoeffector portion of PLAP, molecules having single-chain proteins each of which are fused to an immunoeffector region of TNF or PLAP, and molecules having single-chain proteins only one of which is fused to an immunoeffector polypeptide, particularly an immunoeffector portion of TNF or PLAP.

Without being bound by any particular theory, the inventors speculate on several models which can equally explain the phenomenon of multivalence in antigen-binding fusion proteins. The inventors' models are presented herein for the purpose of illustration only, and are not to be construed as limitations upon the scope of the invention. The invention is useful and operable regardless of the precise mechanism of multivalence.

Figure 1B:
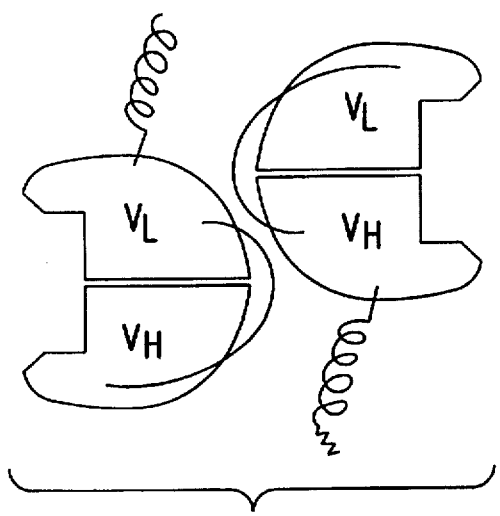
Figure 1C:
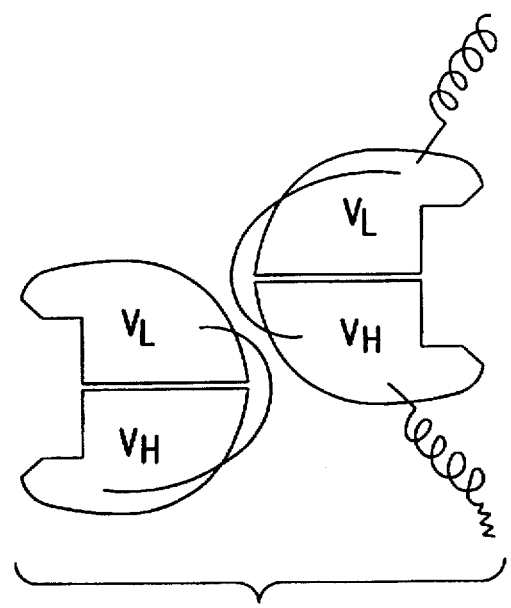
Figure 2A:
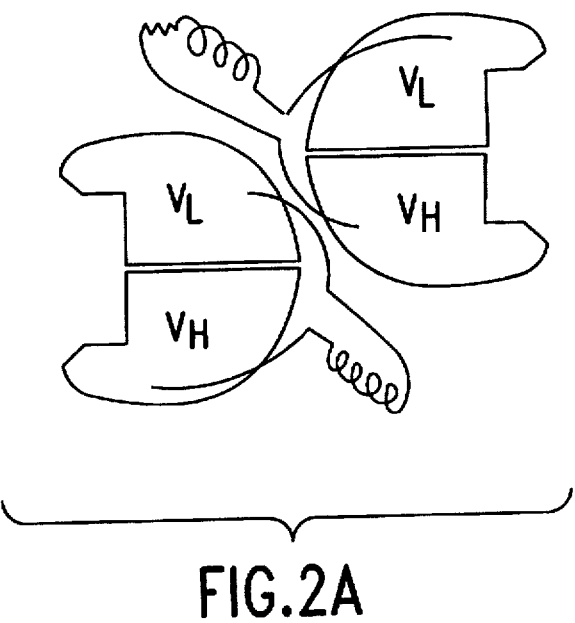
FIGS. 2A–B illustrate a schematic diagram of various monovalent and multivalent antigen-binding fusion molecules.
Figure 2B:
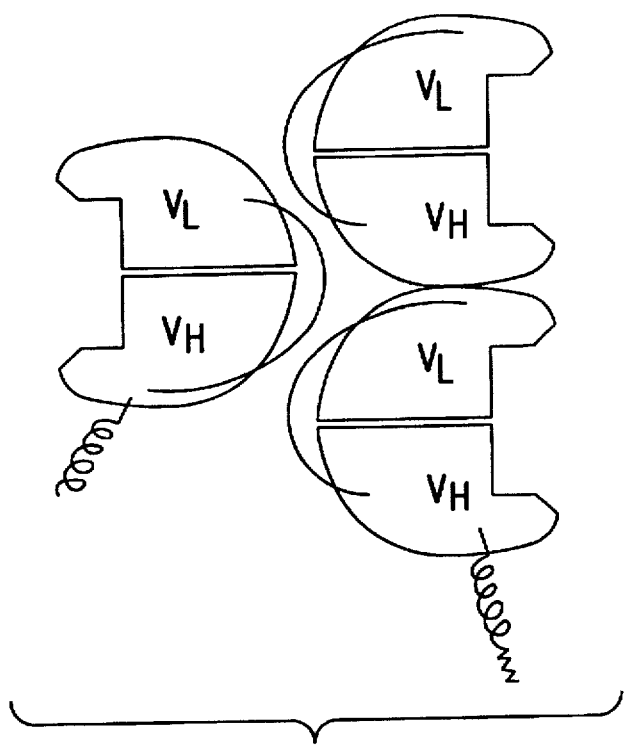

FIG. 1 depicts the first hypothetical model for the creation of a protein, the "Association" model. FIG. 1A shows two monovalent single-chain antigen-binding fusion proteins, each composed of a V$_L$, a V$_H$, and a linker polypeptide covalently bridging the two. Each monovalent single-chain antigen-binding fusion protein is depicted having an identical antigen-binding fusion site containing antigen. FIGS. 1B and 1C show the simple association of the two single-chain antigen-binding fusion proteins to create the bivalent form of the protein. It is hypothesized that simple hydrophobic forces between the monovalent fusion proteins are responsible for their association in this manner. The monovalent units retain their original association between the V$_H$ and V$_L$ regions. Only one of the molecules depicted in FIG. 1C is a fusion molecule. Any number of the single-chain monomeric subunits in a multivalent molecule can be fused to a fusion partner.

Figure 3A:
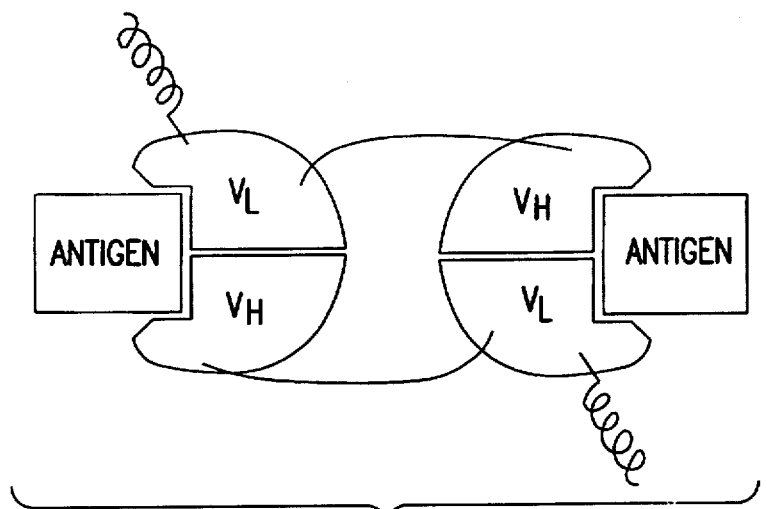
FIGS. 3A–C illustrate a schematic of divalent and trivalent fusion molecules.
Figure 3B:
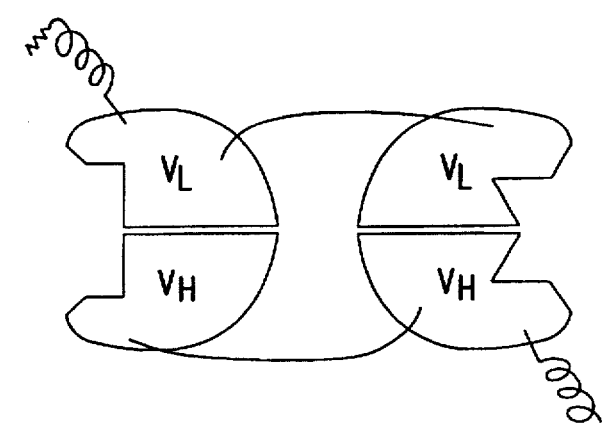

An alternative model for the formation of antigen-binding fusion proteins is shown in FIGS. 3A and 3B. This "Rearrangement" model hypothesizes the dissociation of the variable region interface by contact with dissociating agents such as guanidine hydrochloride, urea, or alcohols such as ethanol, either alone or in combination. Combinations and relevant concentration ranges of dissociating agents are recited in the discussion concerning dissociating agents in U.S. patent application Ser. No. 07/989,846. Subsequent re-association of dissociated regions allows variable region recombination differing from the starting single-chain proteins, as depicted in FIGS. 3A and 3B. The homobivalent fusion antigen-binding fusion protein of FIG. 3A is formed from parent single-chain antigen-binding fusion proteins similar to those shown in FIG. 1A. The recombined bivalent protein has $V_L$ and $V_H$ from the parent monovalent single-chain proteins. The homobivalent fusion protein of FIG. 3A is a depicted as a fully functional monospecific bivalent protein capable of actively binding two antigen molecules.

FIG. 3B shows the formation of heterobivalent antigen-binding fusion proteins via the Rearrangement model. FIG. 3B shows a pair of single-chain proteins, one having two $V_L$ and one having two $V_H$. These single-chain proteins have reduced or no ability to bind antigen because of the mixed nature of their antigen-binding sites, and thus are made specifically to be assembled into proteins through this route. FIG. 3B shows the heterobivalent antigen-binding fusion protein formed whereby the variable regions of the parent proteins are shared between the separate halves of the heterobivalent protein. The Rearrangement model also explains the generation of proteins of a higher order than bivalent, as it can be appreciated that more than a pair of single-chain proteins can be reassembled in this manner.

Figure 3C:
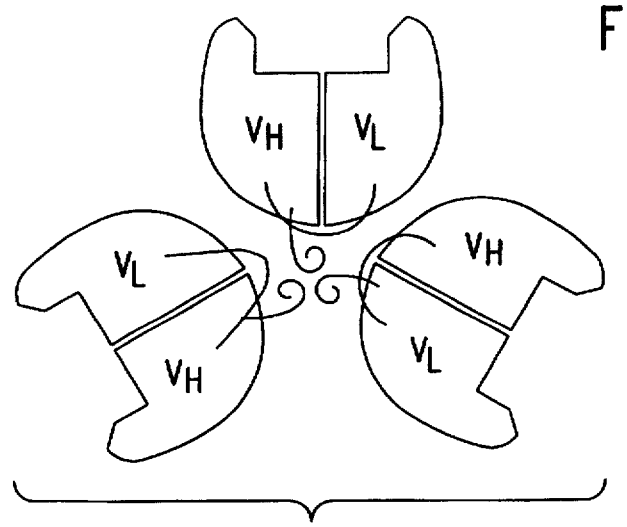

Either the Rearrangement or that Association model can be used to explain the fusion constructs wherein the multivalent molecules are formed by binding between the fusion partner moieties. A specific example of this general multivalent fusion protein is depicted in FIG. 3C. Skilled artisans will immediately recognize that many such multivalent proteins can be constructed using moieties from proteins that are multimeric as the fusion partner. For example, TNF is active as a trimer. An embodiment of the TNF fusion constructs of the invention provides a trivalent molecule that forms a trimer by bonding between the TNF moieties. This type of structure is schematically represented by FIG. 3C.

The limitations of two-dimensional images of three-dimensional objects must be taken into account when considering the structures in the figures. Thus, the actual spatial arrangement of proteins can be expected to vary somewhat from these figures.

VII. Methods of Use of Antigen-Binding Fusion Proteins

The present invention provides uses for treating physiological conditions, such as cancer, by targeting the activities of TNF and PLAP.

The invention also extends to uses for the antigen-binding fusion proteins in purification and biosensors. Affinity purification is made possible by affixing the antigen-binding fusion protein to a support, with the antigen-binding fusion sites exposed to and in contact with the ligand molecule to be separated, and thus purified. Biosensors generate a detectable signal upon binding of a specific antigen to an antigen-binding fusion molecule, with subsequent processing of the signal. Immunoeffector antigen-binding fusion proteins, when used as the antigen-binding fusion molecule in biosensors, may change conformation upon binding, thus generating a signal that may be detected.

Essentially all of the uses for which monoclonal or polyclonal antibodies, or fragments thereof, have been envisioned by the prior art, can be addressed by the proteins of the present invention. These uses include detectably-labelled forms of the protein. Types of labels are well-known to those of ordinary skill in the art. They include radiolabelling, chemiluminescent labeling, fluorochromic labelling, and chromophoric labeling. Other uses include imaging the internal structure of an animal (including a human) by administering an effective amount of a labelled form of the protein and measuring detectable radiation associated with the animal. They also include improved immunoassays, including sandwich immunoassay, competitive immunoassay, and other immunoassays wherein the labelled antibody can be replaced by the antigen-binding fusion protein of this invention. See, for example, Kohler et al., *Nature* 256:495 (1975); Kohler et al., *Eur. J. Immunol.* 6:511 (1976); Kohler et al., *Eur. J. Immunol.* 6:292 (1976); Hammerling et al., In *Monoclonal Antibodies and T-Cell Hybridomas*, pp. 563–681, Elsevier, N (1981); Sambrook et al., *Molecular Cloning—A Laboratory Manual*, (Second Edition), Cold Spring Harbor Labs (1989).

VIII. Genetic Constructs and Gene Expression

The invention also includes a DNA sequence encoding single-chain antigen-binding fusion proteins that can be expressed in a variety of hosts. The genes can be expressed as protein which can be isolated and folded using any method known in the art. It is preferred that the fusion molecules by made as described in U.S. patent application Ser. No. 07/989,846 or U.S. Pat. No. 5,260,203.

Synthesis of DNA sequences is well know in the art, and possible through at least two routes. First, it is well-known that DNA sequences may be synthesized through the use of automated DNA synthesizers de novo, once the primary sequence information is known. Alternatively, it is possible to obtain a DNA sequence coding for a single-chain antigen-binding fusion protein by removing the stop codons from the end of a gene encoding a single-chain antigen-binding protein, and then inserting a spacer and a gene encoding an immunoeffector protein. Example 1 demonstrates the construction of a DNA sequence coding for a single-chain immunoeffector antigen-binding fusion protein. Other methods of genetically constructing single-chain immunoeffector antigen-binding fusion proteins come within the spirit and scope of the present invention.

The transformed cells will be of particular use in expressing significant quantities of immunoeffector antigen-binding fusion proteins which are useful in the immunological methods of the invention (see Example 2). Moreover, one skilled in the art will realize that the fusion proteins of the invention may be readily adapted to many methods known and employed in the art in order to further analyze the effects of the fusion proteins on tumors and tumor cell, and to study the structure of the fusion proteins. For example, the cells lines of the invention can be used with large-scale fermentation apparatus to achieve high yields of protein useful for many purposes, such as, for example, the formation of crystals for crystallographic studies (see, generally, Van Holde, *Physical Biochemistry*, Prentice-Hall, NJ (1972)) and the rational design of therapeutic agents.

IX. Methods of Making Antigen-Binding Fusion Proteins

Single-chain antigen-binding fusion proteins of the invention can be made by any process, but preferably according to the process for making single-chain antigen-binding proteins set forth in U.S. Pat. No. 4,946,778. Briefly, that patent pertains to a single polypeptide chain antigen-binding molecule which has binding specificity and affinity substantially similar to the binding specificity and affinity of the aggregate light and heavy chain variable regions of an antibody, to genetic sequences coding therefore, and to recombinant DNA methods of producing such molecules, and uses for such molecules. The single-chain protein produced by the methodology in U.S. Pat. No. 4,946,778 comprises two regions linked by a linker polypeptide. The two regions are termed the $V_H$ and $V_L$ regions, each region having one half of a functional antigen-binding fusion site.

Multivalent antigen-binding fusion proteins of the invention can be made by any process, but preferably according to the process for making multivalent antigen-binding proteins set forth in U.S. patent application Ser. No. 07/989,846.

The use of the term "substantially free" when used to describe a composition of multivalent single-chain antigen-binding fusion protein molecules means the lack of a significant peak corresponding to the single-chain molecule, when the composition is analyzed by cation exchange chromatography (see U.S. patent application Ser. No. 07/989,846 for a description of these techniques).

Having now generally described this invention the same will better be understood by reference to certain specific examples which are included for purposes of illustration and are not intended to limit it unless otherwise specified.

EXAMPLE 1

Genetic Construction of CC49/212 SCA with C-Terminal PLAP Moiety

Gene constructions of CC49/212 SCA with a PLAP C-terminus were achieved by ligating a synthetic DNA segment corresponding to the encoded PLAP peptide at the 3' end of the CC49/212 gene. Six consecutive oligonucleotides ranging in size from 24 to 29 bases were synthesized on an ABI DNA synthesizer. These oligonucleotides were designed to encode the PLAP peptide in two sets of complementary sequences with three oligonucleotides on each strand of the duplex DNA segment. The complete synthetic fragment with the six annealed oligonucleotides will contain one single stranded overhang corresponding to a cleaved BstEII restriction site, and one single stranded overhang corresponding to a cleaved BamHI restriction site. This strategy allows the direct ligation of the segment into an existing CC49/212 gene which bears these restriction sites at the appropriate locations as seen in FIGS. 4A–B. The oligonucleotides were phosphorylated with ATP plus T4 polynucleotide kinase; annealed to form the duplex fragment by heating the solution to 95° C. for 2 min following by slow cooling to 22° C.; and the synthetic segment was treated with T4 DNA ligase plus the purified CC49/212 M13 vector which also had been digested with BstEII plus BamHI. The ligations were transformed into *E. coli* GX1210 and recombinant plaques were confirmed to have the desired sequence by dideoxy DNA sequencing.

The pGX5410 expression vector contains a bacteriophage OL/PR promoter followed by a signal peptide derived from the *E. coli* ompA gene. The AatII-BamHI fragment from the confirmed CC49/212/PLAP gene construction in M13 was excised by restriction endonuclease digestion, purified by gel electrophoresis on FMC agarose, and ligated into plasmid pGX5410 which had also been digested with AatII plus BamHI. The ligated vector was transformed into competent *E. coli* GX6712 and transformants were analyzed for gene expression using the methods of Whitlow and Filpula, *Methods, Companion Methods Enzymol.* 2:97–105 (1991).

EXAMPLE 2

Transformation of Bacteria With PLAP Fusion Genetic Construct

Gx8962 is a construct having CC49/212 with the twenty-one amino acid of the PLAP fragment attached to the C-terminus of the CC49 at the Bst EII restriction site. Gx8963 is CC49 with the twenty-one amino acid PLAP fragment substituted as the linker between the light chain and heavy chain of CC49. These constructs were created essentially as described in Example 1.

*E. coli* strains transformed with these expression vectors were grown in LB with fifty micrograms per ml ampicillin at 30° C. to mid-log phase, and induced at 42° C. for one hour.

Cell lysates were prepared using standard techniques and run on 14% Tris-glycine acrylamide gels. BRL high molecular weight standards were utilized on these gels. The gel was loaded so that lysates from cells before induction could be compared with lysates from cells following induction for one hour at 42° C. Expression was demonstrated for constructions Gx8962 and Gx8963.

EXAMPLE 3

Tag-72 Binding Activity of PLAP Fusion SCAs By Competition ELISA

The CC49 monoclonal antibody was developed by Dr. Jeffrey Schlom's group at the U.S. National Cancer Institute. This antibody binds specifically to the pan-carcinoma tumor antigen TAG-72. See Muraro et al., *Can. Res.* 48:4588–4596 (1988).

Figure 7:
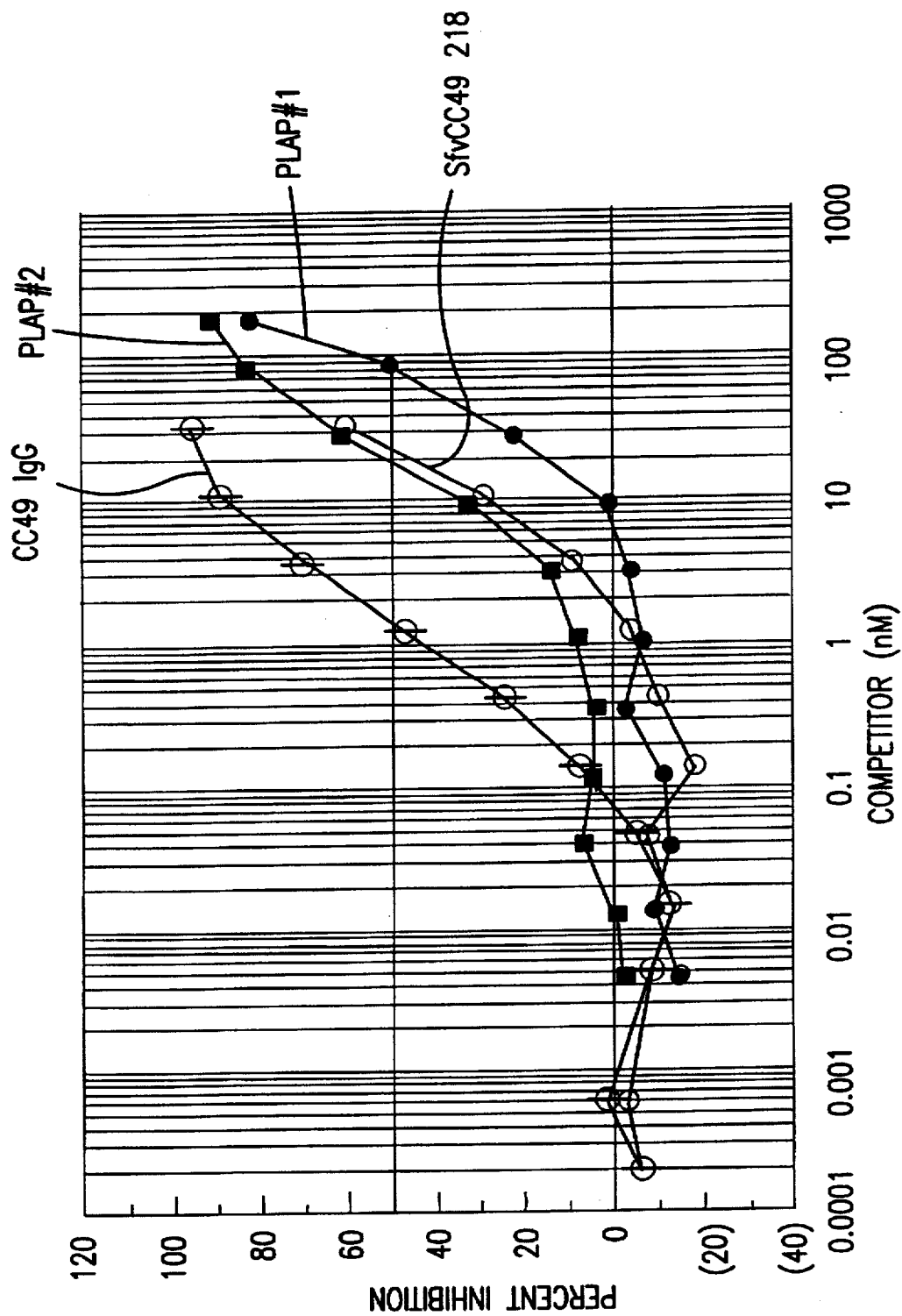
FIG. 7 depicts a competition radioimmunoassay of CC49 IgG ($^{125}$I labeled). CC49 IgG is competed against PLAP No. 1, PLAP No. 2 and CC49/218 SCA (labeled SFv CC49 218). PLAP No. 1 and PLAP No. 2 represent two different preparations of CC49/212 SCA with PLAP C-terminus.

To determine the binding properties of the SCA-PLAP fusion proteins, a competition radioimmunoassay (RIA) was set up in which a CC49 IgG labeled with I-125 is competed against unlabeled SCA-PLAP fusions (CC49/212 C-terminus) for binding to TAG-72 on a human breast carcinoma extract. This competition RIA was used to determine if the fusion SCAs bind to the TAG-72 antigen. FIG. 7 illustrates that PLAP No. 1 and PLAP No. 2 efficiently bind the TAG-72 antigen as compared to positive control, CC49 IgG and SCA CC49/218. PLAP No. 1 and PLAP No. 2 are two purified CC49/212 PLAP C-terminus clones.

All publications cited herein are incorporated fully and in their entirety into this disclosure by reference.

From the foregoing it will be appreciated that, although specific embodiments of the invention have been described herein for purposes of illustration, various modifications may be made without deviating from the spirit and scope of the invention and the following claims. As examples, the steps of the preferred embodiment constitute only one form of carrying out the process in which the invention may be embodied.

---

What is claimed is:

1. An isolated nucleic acid molecule which codes for an immunoeffector antigen-binding fusion protein comprising:
  (a) a first polypeptide comprising the binding portion of the variable region of an antibody heavy or light chain;
  (b) a second polypeptide comprising the binding portion of the variable region of an antibody heavy or light chain;
  (c) a peptide linker linking said first and second polypeptides (a) and (b) into a single-chain molecule; and,
  (d) an immunoeffector polypeptide fused to at least one of said polypeptide of (a), (b) or said peptide (c),
wherein the immunoeffector is Phospholipase A activating protein.

2. An isolated nucleic acid molecule which codes for a cytolytic antigen-binding fusion protein comprising:
  (a) a first polypeptide comprising the binding portion of the variable region of an antibody heavy or light chain;
  (b) a second polypeptide comprising the binding portion of the variable region of an antibody heavy or light chain; and
  (c) a peptide linker linking said first and second polypeptides (a) and (b) into said single-chain molecule; and,
  (d) a cytolytic polypeptide fused to at least one of said polypeptide (a), (b) or said peptide (c);
wherein the cytolytic polypeptide is Phospholipase A activating protein.

3. An isolated nucleic acid molecule which codes for a single-chain fusion protein comprising:
  (a) a first polypeptide comprising the $V_L$ or $V_H$ of a CC49 monoclonal antibody;
  (b) a second polypeptide comprising the $V_L$ or $V_H$ of a CC49 monoclonal antibody;
  (c) a peptide linker linking a first and second polypeptides (a) and (b) into a single-chain protein; and,
  (d) an immunoeffector polypeptide fused to at least one polypeptide of (a), (b) or peptide (c),
wherein said immunoeffector is Phospholipase A activating protein.

4. A DNA molecule comprising the isolated nucleic acid molecule of any one of claims 1, 2, or 3 and a vector.

5. A host cell transformed with the DNA molecule of claim 4.

6. The isolated nucleic acid molecule according to claim 1, wherein said immunoeffector antigen-binding fusion protein further comprises TNF or an immunoeffector fragment of TNF fused to at least one of said polypeptides (a), (b), said peptide (c), or said immunoeffector polypeptide.

7. The isolated nucleic acid molecule according to claim 2, wherein said cytolytic antigen-binding fusion protein further comprises TNF or an immunoeffector fragment of TNF fused to at least one of said polypeptides (a), (b), said peptide (c), or said cytolytic polypeptide.

8. The isolated nucleic acid molecule according to claim 3, wherein said single-chain fusion protein further comprises TNF or an immunoeffector fragment of TNF fused to at least one of said polypeptides (a), (b), said peptide (c), or said immunoeffector polypeptide.

* * * * *